(12) United States Patent
Guerriero et al.

(10) Patent No.: US 6,410,713 B1
(45) Date of Patent: Jun. 25, 2002

(54) DNA ENCODING PROTEINS THAT INHIBIT HSP70 FUNCTION

(76) Inventors: Vincent Guerriero, 1101 E. Paseo Pavon, Tucson, AZ (US) 85718; Deborah A. Raynes, 1971 W. Paseo Cuenca, Tucson, AZ (US) 85704

( * ) Notice: Subject to any disclaimer, the term of this patent is extended or adjusted under 35 U.S.C. 154(b) by 0 days.

(21) Appl. No.: 09/444,336

(22) Filed: Nov. 19, 1999

Related U.S. Application Data

(60) Provisional application No. 60/109,351, filed on Nov. 20, 1998.

(51) Int. Cl.$^7$ .............................................. C07H 21/04
(52) U.S. Cl. ..................... 536/23.5; 435/69.1; 435/70.1; 435/90.1; 514/44; 530/350; 530/412; 530/417; 530/418; 536/23.1
(58) Field of Search ........................... 514/44; 530/350, 530/412, 417, 418; 536/23.1, 23.5; 435/69.1, 70.1, 91.1

(56) References Cited

PUBLICATIONS

Riffkin et al. A single amino acid change between the antigenically different extracellular serine proteases V2 and B2 from Dichelobacter nodosus. Gene (1995) vol. 167, pp 279–283.*
Hillier et al. Generation and Analysis of 280,000 Human Expressed Sequence Tags. Genome Research. Sep. 1996, see pp. 807–827.
Pharmacia Biotech Overview of Molecular Biology Products. 1996, pp. 107, 110–117, 139, 163–165.
Stratagene Cloning Systems. 1994, see pp. 42–43.
Fix, J.A. Oral Controlled Release Technology for Peptides: Status and Future Prospects. Pharmaceutical Research, 1996, vol. 13, No. 12, see pp. 1760–1764.
Takakura et al. Macromolecular Carrier Systems for Targeted Drug Delivery: Pharmacokinetic Considerations on Biodistribution. Pharamceutical Research, 1996, vol. 13, No. 6, pp. 820–831.
S. Lindquist and E.A. Craig, "The Heat Shock Proteins," Annual Revue of Genetics. 22:631–77, 1988.
Hohfeld, Jorg, et al., "Hip, a Novel Cochaperone Involved in the Eukaryotic Hsc70/Hsp40 Reaction Cycle," Cell vol. 83,589–598 (Nov. 17, 1995).
Cyr, D. M. et al., "DnaJ–like Proteins: Molecular Chaperones and Specific Regulators of Hsp70," TIBS 19 (Apr., 1994)
Johnson, B.D., et al., "Hop Modulates Hsp70/Hsp90 Interactions in Protein Folding," JBC 273:6, pp. 3679–3686 (Feb. 6, 1998).
Leung, S.M. and L.E. Hightower, "A 16–kDa Protein Functions as a New Regulatory Protein for Hsc70 Molecular Chaperone and Is Identified as a Member of the Nm23/Nucleoside Disphosphate Kinase Family," JBC 275:5, pp. 2607–2614 (Jan. 31, 1997).

Chamberlain, L.H. and R.D. Burgoyne, "Activation of the ATPase Activity of Heat–Shock Proteins Hsc70/Hsp70 by Cysteine–String Protein," Biochem. J. 322, pp. 853–858 (1997).
Braun, J.E.A., et al., "The Cysteine String Secretory Vesicle Protein Activates Hsc70 ATPase," JBC 271:42, pp. 25989–25993 (Oct. 18, 1996).
Jiang, R.F. et al., "Interaction of Auxilin with the Molecular Chaperone, Hsc70," JBC 272:10, pp. 6141–6145 (Mar. 7, 1997).
Zeiner, M. et al., "Mammalian proten RAP46: an interaction partner and modulator of 70 dDa heat shock proteins," EMBO J. 16:18, pp. 5483–5490 (1997).
Takayama, S. et al., "BAG–1 modulates the chaperone activity of Hsp70/Hsc70," EMBO J. 16:16, pp. 4887–4896 (1997).
V.L. et al., "Hsp70 Prevents Activation of Stress Kinase," JBC 272:29, pp. 18033–18037 (Jul. 18, 1997).
Mosser, D.D., et al., "Role of the Human Heat Shock Protein Hsp70 in Protection Against Stress–Induced Apoptosis," Mol. and Cell. Biol., 17:9, pp. 5317–5327 (Sep., 1997).
Bartel, P.L. et al., "Using the two–hybrid system to detect protein–protein interactions," from "Cellular Interactions in Development: A Practical Approach" (Ed. David Hartley) Oxford University Press (1993).
Berger and Kimmel (1987), "Guide to Molecular Cloning Techniques, Methods in Enzymology," v.152, Academic Press, San Diego, CA).
Sambrook, J. et al., "Molecular Cloning, A Laboratory Manual," Cold Spring Harbor Press, Plainview, N.Y. (1989).
"Remington's Pharmaceutical Sciences" (Maack Publishing Co., Easton, Pa).
Raynes et al., "Inhibition of Hsp70 ATPase Activity and Protein Renaturation by a Novel Hsp70–binding Protein," The Journal of Biological Chemistry, vol. 273, pp. 32883–32888, Dec. 4, 1998.

* cited by examiner

Primary Examiner—Jeffrey Stucker
Assistant Examiner—Ulrike Winkler
(74) Attorney, Agent, or Firm—Gavin J. Milczarek-Desai; Durando Birdwell & Janke

(57) ABSTRACT

Human heat-shock protein-binding proteins (HspBP-1 and HspBP-2) are disclosed with the polynucleotides which identify and encode them. Genetically engineered expression vectors and host cells comprising the nucleic acid sequences encoding heat-shock protein-binding proteins (HspBP) are also disclosed and a method for producing HspBP polypeptides. Also provided is a process of using HspBP for abrogating heat shock-protein activity in the prevention or treatment of diseases associated with such activity.

17 Claims, 9 Drawing Sheets

SEQUENCE LISTING

<160> NUMBER OF SEQ ID NOS: 10

<210> SEQ ID NO 1
<211> LENGTH: 359
<212> TYPE: PRT
<213> ORGANISM: Homo sapiens

<400> SEQUENCE: 1

```
Met Ser Asp Glu Gly Ser Arg Gly Ser Arg Leu Pro Leu Ala Leu Pro
 1               5                   10                  15

Pro Ala Ser Gln Gly Cys Ser Ser Gly Gly Gly Gly Gly Ser Ser
             20                  25                  30

Ala Gly Gly Ser Gly Asn Ser Arg Pro Pro Arg Asn Leu Gln Gly Leu
         35                  40                  45

Leu Gln Met Ala Ile Thr Ala Gly Ser Glu Glu Pro Asp Pro Pro
     50                  55                  60

Glu Pro Met Ser Glu Glu Arg Arg Gln Trp Leu Gln Glu Ala Met Ser
```

-continued

```
                65                  70                  75                  80
Ala Ala Phe Arg Gly Gln Arg Glu Glu Val Glu Gln Met Lys Ser Cys
                    85                  90                  95
Leu Arg Val Leu Ser Gln Pro Met Pro Thr Ala Gly Glu Ala Glu
            100                 105                 110
Gln Ala Ala Asp Gln Gln Glu Arg Glu Gly Ala Leu Glu Leu Leu Ala
            115                 120                 125
Asp Leu Cys Glu Asn Met Asp Asn Ala Ala Asp Phe Cys Gln Leu Ser
        130                 135                 140
Gly Met His Leu Leu Val Gly Arg Tyr Leu Glu Ala Gly Ala Ala Gly
145                 150                 155                 160
Leu Arg Trp Arg Ala Ala Gln Leu Ile Gly Thr Cys Ser Gln Asn Val
                165                 170                 175
Ala Ala Ile Gln Glu Gln Val Leu Gly Leu Gly Ala Leu Arg Lys Leu
            180                 185                 190
Leu Arg Leu Leu Asp Arg Asp Ala Cys Asp Thr Val Arg Val Lys Ala
        195                 200                 205
Leu Phe Ala Ile Ser Cys Leu Val Arg Glu Gln Glu Ala Gly Leu Leu
    210                 215                 220
Gln Phe Leu Arg Leu Asp Gly Phe Ser Val Leu Met Arg Ala Met Gln
225                 230                 235                 240
Gln Gln Val Gln Lys Leu Lys Val Lys Ser Ala Phe Leu Leu Gln Asn
                245                 250                 255
Leu Leu Val Gly His Pro Glu His Lys Gly Thr Leu Cys Ser Met Gly
            260                 265                 270
Met Val Gln Gln Leu Val Ala Leu Val Arg Thr Glu His Ser Pro Phe
        275                 280                 285
His Glu His Val Leu Gly Ala Leu Cys Ser Leu Val Thr Asp Phe Pro
    290                 295                 300
Gln Gly Val Arg Glu Cys Arg Glu Pro Glu Leu Gly Leu Glu Glu Leu
305                 310                 315                 320
Leu Arg His Arg Cys Gln Leu Leu Gln Gln His Glu Glu Tyr Gln Glu
                325                 330                 335
Glu Leu Glu Phe Cys Glu Lys Leu Leu Gln Thr Cys Phe Ser Ser Pro
            340                 345                 350
Ala Asp Asp Ser Met Asp Arg
        355

<210> SEQ ID NO 2
<211> LENGTH: 362
<212> TYPE: PRT
<213> ORGANISM: Homo sapiens

<400> SEQUENCE: 2

Met Ser Asp Glu Gly Ser Arg Gly Ser Arg Leu Pro Leu Ala Leu Pro
1               5                   10                  15
Pro Ala Ser Gln Gly Cys Ser Ser Gly Gly Gly Gly Gly Gly Gly
            20                  25                  30
Gly Ser Ser Ala Gly Gly Ser Gly Asn Ser Arg Pro Pro Arg Asn Leu
        35                  40                  45
Gln Gly Leu Leu Gln Met Ala Ile Thr Ala Gly Ser Glu Glu Pro Asp
    50                  55                  60
Pro Pro Pro Glu Pro Met Ser Glu Glu Arg Gln Trp Leu Gln Glu
65                  70                  75                  80
```

```
Ala Met Ser Ala Ala Phe Arg Gly Gln Arg Glu Glu Val Gln Met
                85                  90                  95

Lys Ser Cys Leu Arg Val Leu Ser Gln Pro Met Pro Thr Ala Gly
            100                 105                 110

Glu Ala Glu Gln Ala Ala Asp Gln Gln Glu Arg Glu Gly Ala Leu Glu
        115                 120                 125

Leu Leu Ala Asp Leu Cys Glu Asn Met Asp Asn Ala Ala Asp Phe Cys
    130                 135                 140

Gln Leu Ser Gly Met His Leu Leu Val Gly Arg Tyr Leu Glu Ala Gly
145                 150                 155                 160

Ala Ala Gly Leu Arg Trp Arg Ala Ala Gln Leu Ile Gly Thr Cys Ser
                165                 170                 175

Gln Asn Val Ala Ala Ile Gln Glu Gln Val Leu Gly Leu Gly Ala Leu
            180                 185                 190

Arg Lys Leu Leu Arg Leu Leu Asp Arg Asp Ala Cys Asp Thr Val Arg
        195                 200                 205

Val Lys Ala Leu Phe Ala Ile Ser Cys Leu Val Arg Glu Gln Glu Ala
    210                 215                 220

Gly Leu Leu Gln Phe Leu Arg Leu Asp Gly Phe Ser Val Leu Met Arg
225                 230                 235                 240

Ala Met Gln Gln Gln Val Gln Lys Leu Lys Val Lys Ser Ala Phe Leu
                245                 250                 255

Leu Gln Asn Leu Leu Val Gly His Pro Glu His Lys Gly Thr Leu Cys
            260                 265                 270

Ser Met Gly Met Val Gln Leu Val Ala Leu Val Arg Thr Glu His
        275                 280                 285

Ser Pro Phe His Glu His Val Leu Gly Ala Leu Cys Ser Leu Val Thr
    290                 295                 300

Asp Phe Pro Gln Gly Val Arg Glu Cys Arg Glu Pro Glu Leu Gly Leu
305                 310                 315                 320

Glu Glu Leu Leu Arg His Arg Cys Gln Leu Leu Gln Gln His Glu Glu
                325                 330                 335

Tyr Gln Glu Glu Leu Glu Phe Cys Glu Lys Leu Leu Gln Thr Cys Phe
            340                 345                 350

Ser Ser Pro Ala Asp Asp Ser Met Asp Arg
        355                 360

<210> SEQ ID NO 3
<211> LENGTH: 1530
<212> TYPE: DNA
<213> ORGANISM: Homo sapiens

<400> SEQUENCE: 3
gacgcggcgc ccagcagagt caggtgcgga cgactttgtc tgtaggagca gcggcggctt      60
gaggacccgg ggagaccctc aagaatcgac ccatcaggac gccagagctg cttcagcggt     120
gaccaccttc tccctctaac acattcttcc cttcttcaca aacggcccat gtcagacgaa     180
ggctcaaggg ggagccgcct gcccctggcg ctgcccccgg cctcccaggg ttgctcttca     240
gggggcggcg gcggcggctc ctcggctggg ggctcgggca attcccggcc ccacgcaac     300 ctccaaggct tgctgcagat ggccatcacc gcgggctctg aagagccaga ccctcctcca     360
gaaccgatga gtgaggagag cgtcagtgg ctgcaggagg ccatgtcggc tgccttccga     420
ggccagcggg aggaggtgga gcagatgaag agctgcctcc gagtgctgtc acagcccatg     480 cccccactg ctggggaggc cgagcaggcg gccgaccagc aagagcgaga gggggccctg     540
```

```
gagctgctgg ccgacctgtg tgagaacatg gacaatgccg cagacttctg ccagctgtct      600
ggcatgcacc tgctggtggg ccggtacctg gaggcggggg ctgcgggact gcggtggcgg      660
gcggcacagc tcatcggcac gtgcagtcag aacgtggcag ccatccagga gcaggtgctg      720
ggcctgggtg ccctgcgtaa gctgctgcgg ctgctggacc gcgacgcctg cgacacggtg      780
cgcgtcaagg ccctcttcgc catctcctgt ctggtccgag agcaggaggc tgggctgctg      840
cagttcctcc gcctggacgg cttctctgtg ttgatgaggg ccatgcagca gcaggtgcag      900
aagctcaagg tcaaatcagc attcctgctg cagaacctgc tggtgggcca ccctgaacac      960
aaagggaccc tgtgctccat ggggatggtc cagcagctgg tggccctggt gcggacagag     1020
cacagcccct ccacgagca cgtgcttgga gccctgtgca gctggtgac agactttccg        1080 cagggtgtgc gcgagtgtcg ggagccggaa ctgggcctgg aggagctcct ccgccaccgc     1140
tgtcagctgc tgcagcagca tgaggagtac caggaggagc tggagttctg tgaaaagctg     1200
ctacagacct gtttctccag cccagcggac gacagcatgg atcggtgaaa ccaggtggct     1260
tcttgccccc ttctccgtgg gaaccccagg cttcttgcct ccctcccac ctacaaggcc      1320 ctctcccaag ggatcgcagg gcctaggtgc ctggacccag ggtgtgccag cccgtctctg     1380
tgcagtccct ggaaggggcg ctgagaaagg caccagctcc ttggacccca cctcccatgc     1440
tctcactctc atccccgttc tcttgtccac acagctcttc aataaaggt gtttctcttc       1500 ctccttctca agaaaaaaaa aaaaaaaaaa                                        1530
```

<210> SEQ ID NO 4
<211> LENGTH: 1617
<212> TYPE: DNA
<213> ORGANISM: Homo sapiens

<400> SEQUENCE: 4

```
ggagcagcgg cggcttgagg acccgggggga gacctcaaga atcgacccat caggacgcca      60
gagctgcttc agcggtgacc accttctccc tctaacacat tcttcccttc ttcacaaacg     120
gcccatgtca gacgaaggct caaggggggag ccgcctgccc ctggcgctgc cccggcctc     180 ccagggttgc tcttcagggg gcggcggcgg cggcggcggc ggctcctcgg ctggggggctc    240 gggcaattcc cggccccccac gcaacctcca aggcttgctg cagatggcca tcaccgcggg    300
ctctgaagag ccagaccctc ctccagaacc gatgagtgag gagaggcgtc agtggctgca    360
ggaggccatg tcggctgcct tccgaggcca gcggaggag gtggagcaga tgaagagctg      420
cctccgagtg ctgtcacagc ccatgccccc cactgctggg gaggccgagc aggcggccga    480
ccagcaagag cgagaggggg ccctggagct gctggccgac ctgtgtgaga acatggacaa    540
tgccgcagac ttctgccagc tgtctggcat gcacctgctg gtgggccggt acctggaggc    600
gggggctgcg ggactgcggt ggcggcggc acagctcatc ggcacgtgca gtcagaacgt     660
ggcagccatc caggagcagg tgctgggcct gggtgccctg cgtaagctgc tgcggctgct    720
ggaccgcgac gcctgcgaca cggtgcgcgt caaggccctc ttcgccatct cctgtctggt   780
ccgagagcag gaggctgggc tgctgcagtt cctccgcctg gacggcttct ctgtgttgat    840
gagggccatg cagcagcagg tgcagaagct caaggtcaaa tcagcattcc tgctgcagaa    900
cctgctggtg ggccaccctg aacacaaagg gaccctgtgc tccatgggga tggtccagca    960
gctggtggcc ctggtgcgga cagagcacag ccccttccac gagcacgtgc ttggagccct   1020
gtgcagcctg gtgacagact ttccgcaggg tgtgcgcgag tgtcgggagc cggaactggg   1080
```

-continued

```
cctggaggag ctcctccgcc accgctgtca gctgctgcag cagcatgagg agtaccagga      1140
ggagctggag ttctgtgaaa agctgctaca gacctgtttc tccagcccag cggacgacag      1200
catggatcgg tgaaaccagg tggcttcttg ccccttctc cgtgggaacc ccaggcctct       1260
tgcctccctc cccacctaca aggccctctc caagggatc gcagggccta ggtgcctgga       1320
cccagggtgt gccagcccgt ctctgtgcag tccctggaag gggcgctgag aaaggcacca     1380
gctccttgga ccccacctcc catgctctca ctctcatccc cgttctcttg tccacacagc      1440
tcttccaata aggtgtttc tcttcctcct tctctccttc actgccgcct ttgtcatctc       1500
ctttggaggg tgcatggggg acgggaggag gggcacgggt ttaagggact ggggagcca       1560 ctggaagaat aataaaagtg ttgctcttta tcaaaaaaaa aaaaaaaaaa aaaaaaa         1617
```

<210> SEQ ID NO 5
<211> LENGTH: 1549
<212> TYPE: DNA
<213> ORGANISM: Mus musculus

<400> SEQUENCE: 5

```
tttaatacga ctcactatag ggaatttggc cctcgaggcc aagaattcgg cacgaggccg       60
gcaagcagac cttcaagagt cgacccatcc ggacaccatt gctgcctcag cggtgaccat      120
caatttcctt taaacacatt cttccttcac agaaagtcca tggcagacaa aggctcaggg     180
ggcagtcgcc tcctcttgc gttgcctccg gcctctcagg gttgctcgtc aggggcagt       240 ggttcctcgg cgggggctc aggcaacccc cggcctccac ggaacctcca aggcctgctg      300
cagatggcta ttactgcggg ttctcaggag ccagaccccc ctccagaacc catgagcgag      360
gagagacgcc aatggctgca ggaagccatg tcggccgcct ccggggcca gcgagaggag      420 gtggagcaga tgaagaactg cctccgggtc ctgtcccagg ccacacccgc aatggctggc      480
gaagctgagc tggccactga ccagcaggag cgtgaaggcg cactagagct gctggcagac      540
ctgtgcgaga acatggacaa tgcagcagat ttctgccagc tgtcaggcat gcatctgctg      600
gtgggtcgat acctggaggc aggggctgca gggctgcgct ggagggcagc acaactcatc      660
ggcacatgca gtcagaacgt tgcagccatc caggagcagg tgttgggctt gggtgccctg      720
cgcaagctac ttcggctgct cgaccggggac tcctgcgaca cggtacgagt caaggctctc    780
ttcgccatct cctgtcttgt ccgagagcag gaggctgggt tgctgcagtt cctccgcctg     840
gatggattct cagtgctgat gcgggccatg cagcagcaag tgcagaagct caaggtcaag     900
tcagcattcc tgctgcagaa cttgctggtg gccaccctg agcacaaagg aacccttgc      960 tccatgggga tggtccagca gctggtggcc cttgtgagga cagaacacag tccttcccat    1020
gagcatgtgc ttggagccct gtgcagcctt gtgacagatt cccctcaggg tgttcgtgaa    1080
tgccgggagc ctgagctggg cctggaggaa ctgctccgcc accgctgcca gctgctgcag    1140
cagcgtgagg agtaccagga ggagctggag ttctgtgaaa agctgttaca gacctgtttc    1200
tctagcccta ccgacgacag catggatcgc tgagaccagg tggcttccttg ctttctctcc    1260 gtgggaaccc caggcctcct gcctccctcc ttccaggca ctctctctta agggattgcc    1320
aggccttgtt tgggctgggt cctggcctg ccagcccatc tctgggtagc ccctggagg      1380 ggttgctgag aaaggtgctg gcccttgat cccctcccctt gctttctgtc atcctttctt    1440
ctcatgtcca cactgctctt caaataaaaa cattctcctg ctcaaaaaaa aaaaaaaaaa    1500 aaagaaacg cggccgcaag cttattccct ttagtgaggg ttaattttt                  1549
```

<210> SEQ ID NO 6
<211> LENGTH: 1465
<212> TYPE: DNA
<213> ORGANISM: Rattus norvegicus

<400> SEQUENCE: 6

| | | | | | |
|---|---|---|---|---|---|
| ggcgtggtgg | ccgctctaga | ccgggcaagc | agaccttaag | gaatcgaccc | atcccgacgc | 60 |
| cagagctgcc | tcaccggtga | ccatcaattt | cttttcaaca | cattcttcct | tcacagacag | 120 |
| tccatggcag | acaaaggctc | aggggcagt | cgcctcccc | tcgcactgcc | tccggcctcc | 180 |
| cagggttgct | cgtcagggag | cagtggctcc | tcggcggggg | gctcaggcaa | ccctcgcctt | 240 |
| ccacggaacc | tccaaggcct | gctgcagatg | gctattactg | cgggctctga | ggaaccagac | 300 |
| cctcctccag | aacccatgag | cgaggagaga | cgccaatggc | tgcaggaagc | catgtcagct | 360 |
| gccttccgag | gccagcggga | agaggtagag | cagatgaaga | actgcctccg | ggtcttgtcc | 420 |
| caggccacac | ccccaactgc | tggtgaagct | gaactggcca | ctgaccagca | ggagcgtgaa | 480 |
| ggggcactag | agctgctggc | agacctgtgc | gagaacatgg | acaatgcggc | agatttctgc | 540 |
| cagctgtcag | gcatgcacct | gctggtgggt | cgatacctgg | aggcaggagc | tgcagggctg | 600 |
| cgttggaggg | cagcacagct | catcggcacg | tgcagtcaga | atgttgcagc | catccaggag | 660 |
| caggtgttgg | gcttgggtgc | cctgcgtaag | ctacttcggc | tgctcgaccg | ggactcctgc | 720 |
| gacacggtac | gagtcaatgc | tctcttcgcc | atctcctgtc | ttgtccgaga | gcaggaggct | 780 |
| ggattgctgc | agttcctccg | cctggatgga | ttctcagtgc | tgatgcgggc | catgcagcag | 840 |
| caagtgcaga | agctcaaggt | caagtcagca | ttcctgctgc | agaacctgct | ggtgggccac | 900 |
| cctgagcaca | aaggaaccct | ttgctccatg | gggatggtcc | agcagctggt | ggcccttgtg | 960 |
| aggacagaac | acagtccttt | ccatgagcat | gtgcttggag | ccctgtgcag | ccttgtgaca | 1020 |
| gacttccctc | aggtgttcg | agaatgccgg | gagcctgagc | tgggcctgga | ggaactgctc | 1080 |
| cgtcatcgct | gccagctgct | gcagcagcat | gaggagtacc | aggaggagct | ggagttctgt | 1140 |
| gaaaagctgt | tacagacctg | tttctccagc | cctacgatg | acagcatgga | tcggtgagac | 1200 |
| caggcggctt | cttgcattct | ctccgtggga | accccaggcc | tcctgcctcc | ctccttccca | 1260 |
| ggcaccctct | cccaagggat | tgccaggcct | tgtttgggcc | tgcgcctggg | cctgccagcc | 1320 |
| catctctagg | cagcccctg | gagggttgc | tgagaaaggt | gctggtccct | tggaaccct | 1380 |
| tccttgcttt | ctgtctttca | tgtccacact | gctcttcaaa | taaaaacatt | tctcctgctc | 1440 |
| aaaaaaaaaa | aaaaaaaaaa | aaaaa | | | | 1465 |

<210> SEQ ID NO 7
<211> LENGTH: 1895
<212> TYPE: DNA
<213> ORGANISM: Brachydanio rerio (zebra fish)

<400> SEQUENCE: 7

| | | | | | |
|---|---|---|---|---|---|
| ccacgcgtcc | ggtttataat | aacggagctg | aactgaactc | aagtgtaaca | ttatttacac | 60 |
| tgcgggaaa | cttgacacac | gtccaagtaa | cgtctgctgc | tactgctaaa | tcggacacac | 120 |
| agcatttaaa | aagatggctg | aaggcacagg | taaccggcat | caccctcgta | atctgcaagg | 180 |
| tgttcttcag | atggcagtgg | aggccggttc | tgcttctgac | ggtccagctc | cgctagaacc | 240 |
| catgacacaa | gagaggatgg | attttctgcg | aggagctctt | tctgaagtgt | gtaaaggaca | 300 |
| aatggatgag | gtcgagcaga | tgaagcgtg | tttggaggtg | ctgaaaactg | atggatgcaa | 360 |
| ggacagagaa | gtcgaaggag | aggaggagga | ggaggaggac | gacgagcggg | aagaagcgct | 420 |

-continued

```
ggaaatgctt tctgagcttt gcgaaaacct ggacaatgca agagatctga tgaagctggg      480
tggtctggat ctgtgtttgt cacggtgtct ctgtcacaca gagacaggca ttcgctggag      540
agcagctcag cttatcgcca gctcggccca gaatatgccg gaggtgcagt tctacctgct      600
taaccagggg gcgctgctaa ccctcctgca gctcgcagat aatgacccac acagcacagt      660
cagggttaaa gcactctacg ccgtgtcctg tttagtgcgt gaacaggaag caggactgaa      720
ggacttcctt tcacatgacg gcttttccgt gctgatgagg gggatgcagt cagacagtga      780
gaagctgaga actaaatcag cgtttcttct tctaaacctt ttgaacagtc atccagaaca      840
caaagatacg gtgttatcta tgggaatggt ccagcagctg gtgtctgttc tccgctctcc      900
tcattcctct gttcacgaac atgtgcttgg cgccctctgc tgtctagtgg aggactctcc      960
ccgtggcatg agcgactgca gagatccatc gctgggcttg gaggaactgc tcaaacagag     1020
agtgcaggat ctaaggggcc aagaggagag cctggaggaa ctggagtttt gtgaacgttt     1080
gcgagcggtt tgttttccgg gacaaacgca agaggataat gctatggatc gctgaccatc     1140
tgattgctga ttcaacgaaa aacagcaaca cccagtttgt attccttctc tgtttaagag     1200
agaaaccaaa acaataggaa taatactgtt aaaaagatca acgtgaaaga gacttttaac     1260
tctgagtttt cagagatgag tttagctgtg tgtgtgtgca tgtgtgcgtg cgtgcgtgtg     1320
ttcatgtgca aactcattta ctggagacaa accctcatgt gtaatgatga tgaacatgta     1380 catttgtttta taatatcttt gttcgttatt ataaatgttc tgttatatgg tcaactttcg     1440
aaacattctt aaagggacag tactctcaaa atgcagtcc tgtcatttgt tctcacttaa      1500
ctcttgagtt tcctctgaac ataaaagaag atattttaat tcatccggtg acttccattg     1560
taatttgttg tcctactata gaagtcagtg ggtaccagca ttcttcaaac tatcttcttt     1620
tgcattcaag aaagaagaaa gaagttcatc aagatttaaa accacataat agaaagtaaa     1680
taatgagata tttgacattt ttgggtgaac tatctcttgg tcaatcacac aaatacaaag     1740
ccataatgta gaactgcaca ttattataat agacaataat taaaaataaa cacattcaga     1800
cctgtgtttt aacaaaaaaa aaaaaaaaa aaaaaaaaaa aaaaaaaaaa aaaaaaaaaa     1860
aaaaaaaaaa aaaaaaaaaa aaaaaaaaaa aaaaa                                1895
```

<210> SEQ ID NO 8
<211> LENGTH: 357
<212> TYPE: PRT
<213> ORGANISM: Mus musculus

<400> SEQUENCE: 8

```
Met Ala Asp Lys Gly Ser Gly Gly Ser Arg Leu Pro Leu Ala Leu Pro
 1               5                  10                  15

Pro Ala Ser Gln Gly Cys Ser Ser Gly Gly Ser Gly Ser Ser Ala Gly
            20                  25                  30

Gly Ser Gly Asn Pro Arg Pro Pro Arg Asn Leu Gln Gly Leu Leu Gln
        35                  40                  45

Met Ala Ile Thr Ala Gly Ser Gln Glu Pro Asp Pro Pro Glu Pro
    50                  55                  60

Met Ser Glu Glu Arg Arg Gln Trp Leu Gln Glu Ala Met Ser Ala Ala
65                  70                  75                  80

Phe Arg Gly Gln Arg Glu Glu Val Glu Gln Met Lys Asn Cys Leu Arg
                85                  90                  95

Val Leu Ser Gln Ala Thr Pro Ala Met Ala Gly Glu Ala Glu Leu Ala
            100                 105                 110
```

-continued

Thr Asp Gln Gln Glu Arg Glu Gly Ala Leu Glu Leu Leu Ala Asp Leu
            115                 120                 125

Cys Glu Asn Met Asp Asn Ala Ala Asp Phe Cys Gln Leu Ser Gly Met
    130                 135                 140

His Leu Leu Val Gly Arg Tyr Leu Glu Ala Gly Ala Ala Gly Leu Arg
145                 150                 155                 160

Trp Arg Ala Ala Gln Leu Ile Gly Thr Cys Ser Gln Asn Val Ala Ala
                165                 170                 175

Ile Gln Glu Gln Val Leu Gly Leu Gly Ala Leu Arg Lys Leu Leu Arg
            180                 185                 190

Leu Leu Asp Arg Asp Ser Cys Asp Thr Val Arg Val Lys Ala Leu Phe
        195                 200                 205

Ala Ile Ser Cys Leu Val Arg Glu Gln Glu Ala Gly Leu Leu Gln Phe
    210                 215                 220

Leu Arg Leu Asp Gly Phe Ser Val Leu Met Arg Ala Met Gln Gln Gln
225                 230                 235                 240

Val Gln Lys Leu Lys Val Lys Ser Ala Phe Leu Leu Gln Asn Leu Leu
                245                 250                 255

Val Gly His Pro Glu His Lys Gly Thr Leu Cys Ser Met Gly Met Val
            260                 265                 270

Gln Gln Leu Val Ala Leu Val Arg Thr Glu His Ser Pro Phe His Glu
        275                 280                 285

His Val Leu Gly Ala Leu Cys Ser Leu Val Thr Asp Phe Pro Gln Gly
    290                 295                 300

Val Arg Glu Cys Arg Glu Pro Glu Leu Gly Leu Glu Leu Leu Arg
305                 310                 315                 320

His Arg Cys Gln Leu Leu Gln Arg Glu Glu Tyr Gln Glu Glu Leu
                325                 330                 335

Glu Phe Cys Glu Lys Leu Leu Gln Thr Cys Phe Ser Ser Pro Thr Asp
            340                 345                 350

Asp Ser Met Asp Arg
        355

<210> SEQ ID NO 9
<211> LENGTH: 357
<212> TYPE: PRT
<213> ORGANISM: Rattus norvegicus

<400> SEQUENCE: 9

Met Ala Asp Lys Gly Ser Gly Ser Arg Leu Pro Leu Ala Leu Pro
1               5                   10                  15

Pro Ala Ser Gln Gly Cys Ser Ser Gly Ser Ser Gly Ser Ser Ala Gly
            20                  25                  30

Gly Ser Gly Asn Pro Arg Leu Pro Arg Asn Leu Gln Gly Leu Leu Gln
        35                  40                  45

Met Ala Ile Thr Ala Gly Ser Glu Glu Pro Asp Pro Pro Glu Pro
    50                  55                  60

Met Ser Glu Glu Arg Arg Gln Trp Leu Gln Ala Met Ser Ala Ala
65                  70                  75                  80

Phe Arg Gly Gln Arg Glu Glu Val Glu Gln Met Lys Asn Cys Leu Arg
                85                  90                  95

Val Leu Ser Gln Ala Thr Pro Pro Thr Ala Gly Glu Ala Glu Leu Ala
            100                 105                 110

Thr Asp Gln Gln Glu Arg Glu Gly Ala Leu Glu Leu Leu Ala Asp Leu
        115                 120                 125

```
Cys Glu Asn Met Asp Asn Ala Ala Asp Phe Cys Gln Leu Ser Gly Met
            130                 135                 140

His Leu Leu Val Gly Arg Tyr Leu Glu Ala Gly Ala Ala Gly Leu Arg
145                 150                 155                 160

Trp Arg Ala Ala Gln Leu Ile Gly Thr Cys Ser Gln Asn Val Ala Ala
                165                 170                 175

Ile Gln Glu Gln Val Leu Gly Leu Gly Ala Leu Arg Lys Leu Leu Arg
            180                 185                 190

Leu Leu Asp Arg Asp Ser Cys Asp Thr Val Arg Val Asn Ala Leu Phe
            195                 200                 205

Ala Ile Ser Cys Leu Val Arg Glu Gln Glu Ala Gly Leu Leu Gln Phe
            210                 215                 220

Leu Arg Leu Asp Gly Phe Ser Val Leu Met Arg Ala Met Gln Gln Gln
225                 230                 235                 240

Val Gln Lys Leu Lys Val Lys Ser Ala Phe Leu Leu Gln Asn Leu Leu
                245                 250                 255

Val Gly His Pro Glu His Lys Gly Thr Leu Cys Ser Met Gly Met Val
                260                 265                 270

Gln Gln Leu Val Ala Leu Val Arg Thr Glu His Ser Pro Phe His Glu
            275                 280                 285

His Val Leu Gly Ala Leu Cys Ser Leu Val Thr Asp Phe Pro Gln Gly
            290                 295                 300

Val Arg Glu Cys Arg Glu Pro Glu Leu Gly Leu Glu Glu Leu Leu Arg
305                 310                 315                 320

His Arg Cys Gln Leu Leu Gln Gln His Glu Glu Tyr Gln Glu Glu Leu
                325                 330                 335

Glu Phe Cys Glu Lys Leu Leu Gln Thr Cys Phe Ser Ser Pro Thr Asp
                340                 345                 350

Asp Ser Met Asp Arg
            355

<210> SEQ ID NO 10
<211> LENGTH: 333
<212> TYPE: PRT
<213> ORGANISM: Brachydanio rerio (zebra fish)

<400> SEQUENCE: 10

Met Ala Glu Gly Thr Gly Asn Arg His His Pro Arg Asn Leu Gln Gly
  1               5                  10                  15

Val Leu Gln Met Ala Val Glu Ala Gly Ser Ala Ser Asp Gly Pro Ala
             20                  25                  30

Pro Leu Glu Pro Met Thr Gln Glu Arg Met Asp Phe Leu Arg Gly Ala
         35                  40                  45

Leu Ser Glu Val Cys Lys Gly Gln Met Asp Glu Val Glu Gln Met Lys
     50                  55                  60

Arg Cys Leu Glu Val Leu Lys Thr Asp Gly Cys Lys Asp Arg Glu Val
 65                  70                  75                  80

Xaa Gly Glu Glu Glu Glu Glu Asp Xaa Xaa Arg Glu Glu Ala Leu
                 85                  90                  95

Glu Met Leu Ser Glu Leu Cys Glu Asn Leu Asp Asn Ala Arg Asp Leu
            100                 105                 110

Met Lys Leu Gly Gly Leu Asp Leu Cys Leu Ser Arg Cys Leu Cys His
        115                 120                 125

Thr Glu Thr Gly Ile Arg Trp Arg Ala Ala Gln Leu Ile Ala Ser Ser
```

-continued

```
              130                 135                 140
Ala Gln Asn Met Pro Glu Val Gln Phe Tyr Leu Leu Asn Gln Gly Ala
145                 150                 155                 160

Leu Leu Thr Leu Leu Gln Leu Ala Asp Asn Asp Pro His Ser Thr Val
                165                 170                 175

Arg Val Lys Ala Leu Tyr Ala Val Ser Cys Leu Val Arg Glu Gln Glu
                180                 185                 190

Ala Gly Leu Lys Asp Phe Leu Ser His Asp Gly Phe Ser Val Leu Met
            195                 200                 205

Arg Gly Met Gln Ser Asp Ser Glu Lys Leu Arg Thr Lys Ser Ala Phe
        210                 215                 220

Leu Leu Leu Asn Leu Leu Asn Ser His Pro Glu His Lys Asp Thr Val
225                 230                 235                 240

Leu Ser Met Gly Met Val Gln Gln Leu Val Ser Val Leu Arg Ser Pro
                245                 250                 255

His Ser Ser Val His Glu His Val Leu Gly Ala Leu Cys Cys Leu Val
                260                 265                 270

Glu Asp Ser Pro Arg Gly Met Ser Asp Cys Arg Asp Pro Ser Leu Gly
            275                 280                 285

Leu Glu Glu Leu Leu Lys Gln Arg Val Gln Asp Leu Arg Gly Gln Glu
        290                 295                 300

Glu Ser Leu Glu Glu Leu Glu Phe Cys Glu Arg Leu Arg Ala Val Cys
305                 310                 315                 320

Phe Pro Gly Gln Thr Gln Glu Asp Asn Ala Met Asp Arg
                325                 330
```

DNA ENCODING PROTEINS THAT INHIBIT HSP70 FUNCTION

CROSS-REFERENCE TO RELATED APPLICATIONS

This application is based on U.S. Provisional Application No. 60/109,351, entitled "Inhibition of HSP 70 ATPase Activity and Protein Renaturation By A Novel HSP-Binding Protein," filed by the same inventors on Nov. 20, 1998.

BACKGROUND OF THE INVENTION

1. Field of Invention

This invention generally relates to the field of molecular medicine and in particular to a novel set of heat-shock protein-binding proteins, and to polynucleotides encoding them, useful in the regulation of physiological events in which one or more 70 kiloDalton heat-shock proteins (Hsp70) are involved, such as normal development, cellular stress responses, heart disease, and cancer.

2. Description of the Related Art

Practically all organisms respond to heat by inducing the synthesis of a group of proteins called the heat-shock proteins. Although the details of this response vary among organisms, the involvement of Hsp70 and Hsp90 gene families is known to be highly conserved. More recently, it has come to be known that heat shock proteins can be induced by a variety of stress-related stimuli besides heat: anoxia, ethanol and certain heavy metal ions also stimulate increased expression and activity by these proteins. Hence, such proteins commonly are more broadly referred to by those in the art as heat stress or, simply, stress proteins.

Interestingly, stress proteins also are present within cells under non-stressful conditions (i.e. under normal physiological conditions). Genetic studies in bacteria and lower eukaryotes have demonstrated that Hsp70 is essential for growth at either high or normal temperatures, indicating a crucial role in normal cellular physiology. See generally S. Lindquist and E. A. Craig, The Heat Shock Proteins, Annual Revue of Genetics. 22:631–77 (1988).

Particular attention has been focused on Hsp70, a member of a multigene family whose genes are expressed under a wide variety of environmental conditions and are found in all cells. As shown schematically in FIG. 1, Hsp70 and related proteins (such as Hsp72, Hsc70, and Grp78) contain an ATPase domain, a substrate binding domain, and a coupling domain. S. Lindquist and E. A. Craig, Annual Revue of Genetics. 22:631–77 (1988).

In terms of function, studies have shown that Hsp70 plays a role in DNA replication, transport of proteins across membranes, binding of proteins to the endoplasmic reticulum, and uncoating clathrin coated vesicles. S. Lindquist and E. A. Craig, Annual Revue of Genetics. 22:631–77 (1988). Furthermore, Hsp70 is known to associate with nonsterified fatty acids, palmitic acid, stearic acid, and myristic acid and to be involved in signal transduction pathways in the cytoplasm. Hohfeld, Jorg, et al., Hip, a Novel Cochaperone Involved in the Eukaryotic Hsc70/Hsp40 Reaction Cycle. Cell vol. 83, 589–598 (Nov. 17, 1995).

Of these functions, perhaps the best studied has been the role of Hsp70 as a "chaperone," a protein that stabilizes other proteins against aggregation and that mediates the folding of newly translated polypeptides in the cytosol and organelles. Proper functioning of Hsp70 as a protein chaperone is dependent on its bound nucleotide state. Specifically, the ATP form of Hsp70 binds substrate very poorly and therefore must be converted to the ADP form before the misfolded protein can bind. Then, the high affinity of Hsp70 for ATP is utilized to "power" the protein folding and other functions of Hsp70, as much energy is generated by the hydrolysis of bound ATP.

The search for regulators of Hsp70 chaperone function has revealed regulatory factors that form complexes with Hsp70 and assist in determining those substrates with which Hsp70 can associate. For example, the DNAJ-like proteins bind protein substrates exhibiting secondary and tertiary structure but have very low affinity for polypeptides in unfolded conformations. On the other hand, Hsp70 proteins bind unfolded proteins best. Thus, by forming a complex with DNAJ-like protein, Hsp70 proteins can bind with many other proteins of varying conformation. Cyr, D. M. et al., DnaJ-like Proteins: Molecular Chaperones and Specific Regulators of Hsp70. TIBS 19 (April, 1994).

Other factors can regulate the substrate binding stability or ATPase activity of Hsp70. Hsp40 stimulates the ATPase of Hsp70 and therefore results in production of the ADP form of Hsp70, which facilitates binding to substrate. Another Hsp70 regulator, the Hip co-chaperone protein, binds to the ATPase domain of Hsp70, thereby promoting the assembly of chaperone complexes and prolonging the time window during which a Hsp70 protein can interact stably with unfolded polypeptides. Hohfeld, Jorg, et al., Hip, a Novel Cochaperone Involved in the Eukaryotic Hsc70/Hsp40 Reaction Cycle. Cell vol. 83, 589–598 (Nov. 17, 1995). Similarly, a regulator named Hop modulates the binding of Hsp70 to Hsp90, thereby stimulating Hsp70-mediated refolding of a denatured protein. Johnson, B. D., et al., Hop Modulates Hsp70/Hsp90 Interactions in Protein Folding. JBC 273:6, pp. 3679–3686 (Feb. 6, 1998).

A potential regulator of Hsp70 is a 16-kDa protein that is a member of the Nm23/nucleoside diphosphate kinase family. This regulator monomerized Hsc70 (a protein closely related to Hsp70) and assisted in releasing Hsc70 from bound substrate. Leung, S. M. and L. E. Hightower, A 16-kDa Protein Functions as a New Regulatory Protein for Hsc70 Molecular Chaperone and Is Identified as a Member of the Nm23/Nucleoside Diphosphate Kinase Family. JBC 272:5, pp. 2607–2614 (Jan. 31, 1997). Also, the cysteine string protein, which is a secretory vesicle protein, and auxilin, a clathrin-associated protein, can both activate Hsc70 ATPase activity. Chamberland, L. H. and R. D. Burgoyne, Activation of the ATPase activity of heat-shock proteins Hsc70/Hsp70 by cysteine-string protein. Biochem. J. 322, pp. 853–858 (1997); Braun, J. E. A., et al., The Cystein String Secretory Vesicle Protein Activates Hsc70 ATPase. JBC 271:42, pp.25989–25993 (Oct. 18, 1996); Jiang, R. F. et al., Interaction of Auxilin with the Molecular Chaperone, Hsc70. JBC 272:10, pp. 6141–6145 (Mar. 7, 1997).

Still other regulators of Hsp70 inhibit Hsp70-mediated refolding. The RAP/HAP46 proteins, which inhibit binding of misfolded proteins to Hsp70, and BAG-1, which causes the release of ADP from Hsp70, both down-regulate Hsp70 activity. Zeiner, M. et al., Mammalian protein RAP46: an interaction partner and modulator of 70 dDa heat shock proteins. EMBO J. 16:18, pp. 5483–5490 (1997); Takayama, S. et al., BAG-1 modulates the chaperone activity of Hsp70/Hsc70. EMBO J. 16:16, pp. 4887–4896 (1997).

Despite the fact that regulators of Hsp70 protein binding have been discovered and characterized, the functional regulation of Hsp70 is not yet understood. Moreover, the ability to directly abrogate or eliminate Hsp70 ATPase activity through a selectively binding protein has not previously been known. Therefore, the discovery and isolation of polynucleotides encoding two isoforms of a human heat-shock protein binding protein (HspBP-1 and HspBP-2), is desirable because they provide a means to investigate the effects of heat shock-protein regulation. Such regulation may have consequences in physiological pathways or conditions in which Hsp70 is known to be involved, such as development, apoptosis, cellular stress, heart disease, and cancer.

BRIEF SUMMARY OF THE INVENTION

It is an object of the invention to provide the cloned polynucleotide sequences encoding novel human heat-shock protein-binding proteins.

A second object of the invention is to provide the deduced polypeptide sequences according to the cloned polynucleotide sequences encoding novel human heat-shock protein-binding proteins.

Another object of the invention is to provide rat, mouse, and zebrafish gene homologues of novel human heat-shock protein-binding proteins.

Still another object of the invention is to provide a means of inhibiting the activity of Hsp70 and related proteins using novel heat-shock protein-binding proteins.

Yet another object of the invention is to provide a means of inhibition of the apoptotic activity of Hsp70 and related proteins using novel heat-shock protein-binding proteins.

In accordance with these objectives, the invention features substantially purified human heat-shock protein-binding proteins (HspBP), designated HspBP-1 and HspBP-2, having the amino acid sequence shown in SEQ ID NO:1 and in SEQ NO:2, respectively. Furthermore, the invention features isolated and substantially purified polynucleotides that encode HspBP-1 or HspBP-2 having the nucleotide sequence shown in SEQ ID NO:3 and SEQ ID NO:4, respectively. Moreover, the invention features nucleic acid sequences encoding polypeptides, oligonucleotides, peptide nucleic acids, fragments, portions or antisense molecules thereof, and expression vectors and host cells comprising polynucleotides that encode human HspBP and its mouse (HspBPM; SEQ ID NO:5), rat (HspBPR; SEQ ID NO:6), and zebrafish (HspBPF; SEQ ID NO:7) homologues. Finally, the invention features pharmaceutical compositions comprising substantially purified HspBP.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiments and particularly pointed out in the claims. However, such drawings and description disclose only some of the various ways in which the invention may be practiced.

BRIEF DESCRIPTION OF THE DRAWINGS

FIGS. 2A and 2B shows the amino acid sequence alignments among human HspBP-1 (SEQ ID NO:1) and HspBP-2 (SEQ ID NO:2) and the homologous mouse (HspBPM; SEQ ID NO:8), rat (HspBPR; SEQ ID NO:9), and zebrafish (HspBPF; SEQ ID NO:10) heat-shock protein binding proteins. Amino acid sequence identity among species is highlighted in black. Small stars (*) below residues indicate conservation of any amino acid among all species, while large stars (☆) above residues indicate conservation of the amino acid cysteine (C) among all species. When four of the five amino acids for a particular position are identical, a period (.) or a colon (:) below a residue indicate the degree to which chemical properties, such as size and charge, are shared between the identical and non-identical residues, with a period indicating partial chemical relatedness and a colon indicating high chemical relatedness. The dashes (-) indicate that a protein lacks an amino acid at that particular position of the alignment.

Figure 8:
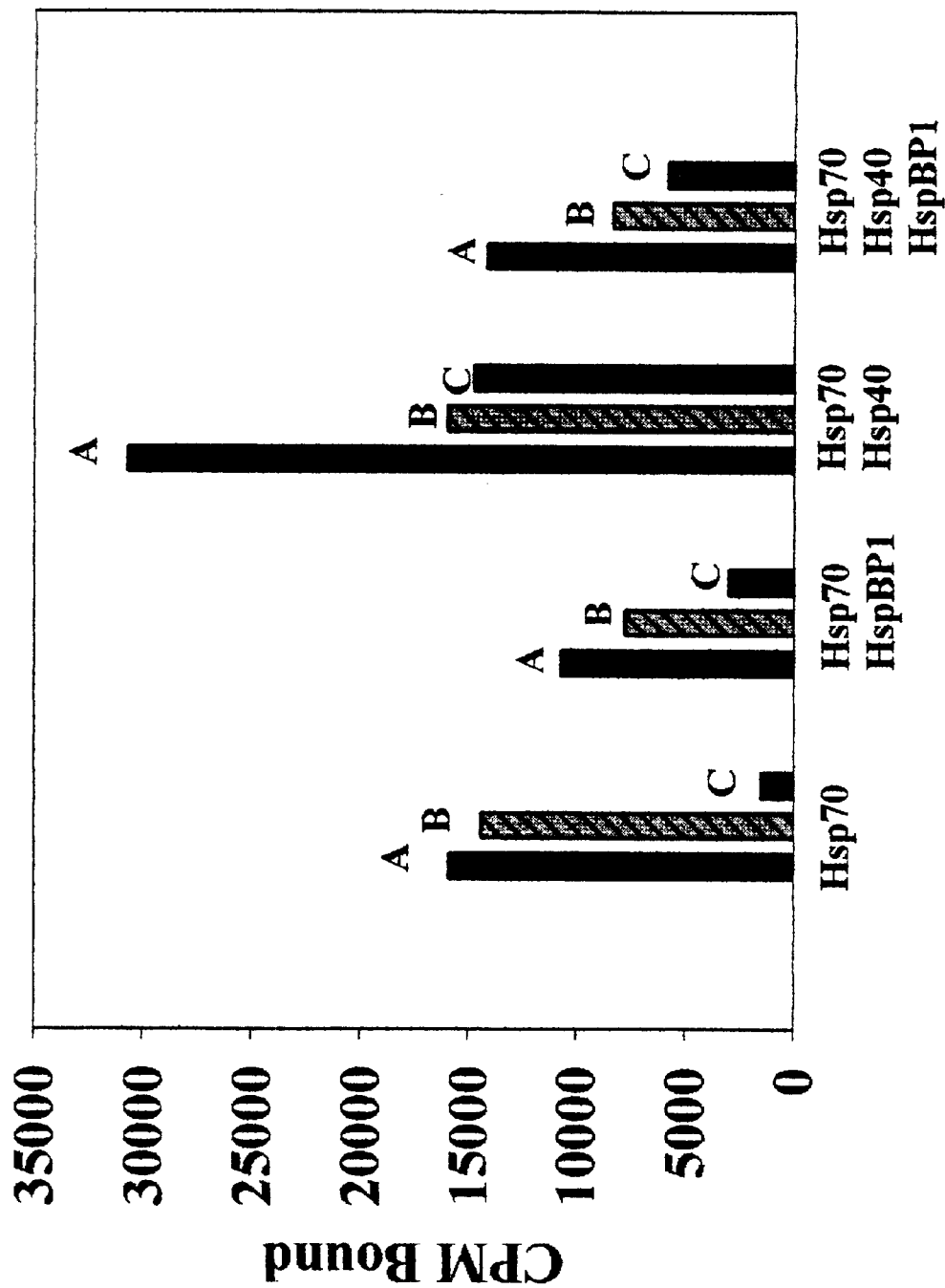

FIG. 8 shows the inhibition of nucleotide binding by HspBP1. Samples were prepared as described for the ATPase assays using 20 μM [α-$^{35}$S]ATP and 12 μM HspBP1. Samples were removed (10 μl) after 10 min. of incubation and unbound nucleotides were removed using spin columns. Bound nucleotides were processed as described above to separate ATP from ADP. A, total nucleotide bound; B, ATP bound; C, ADP bound.

Figure 9:
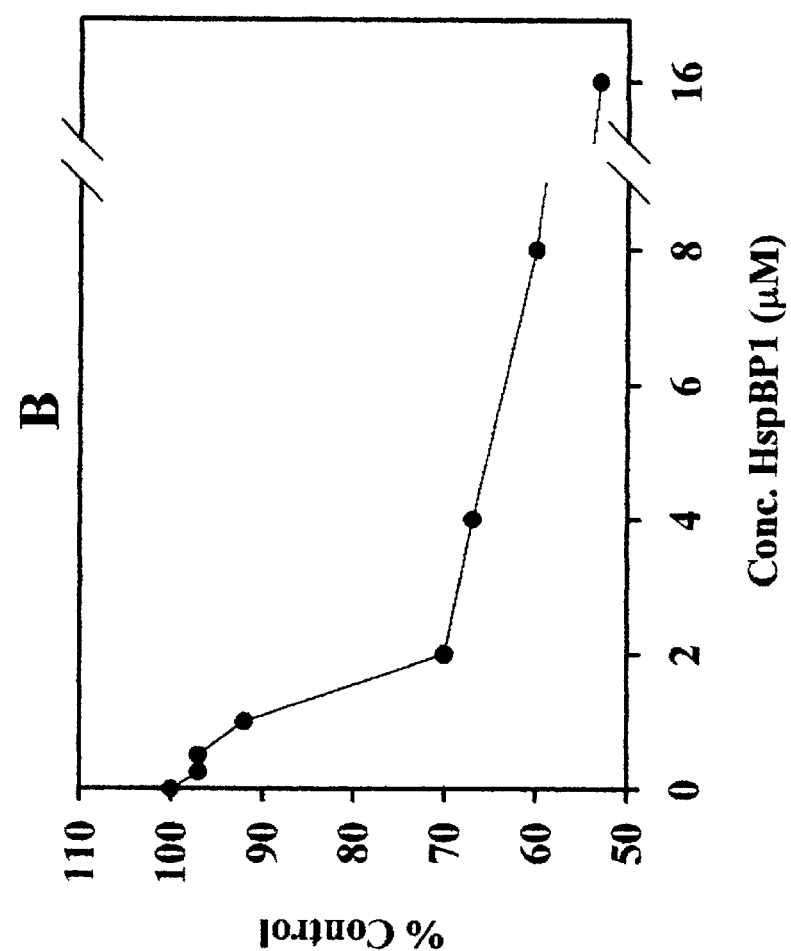
Figure 9:
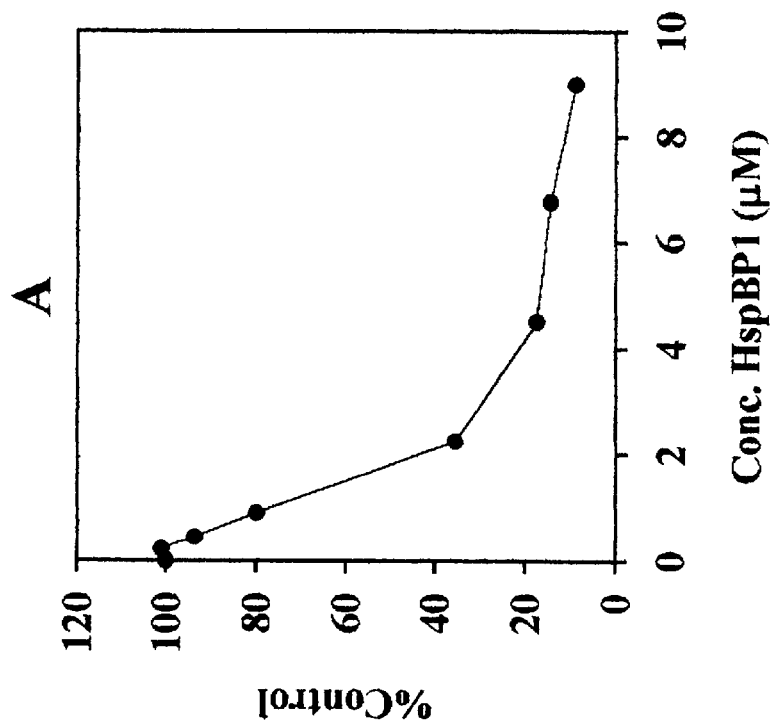

FIG. 9 shows luciferase renaturation inhibition by HspBP1. Luciferase was denatured by heating and then placed on ice. The denatured enzyme was added to either rabbit reticulocyte lysate (A) or a defined system containing Hsp70, Hsp40 and Hsp90 (B) in the absence or presence of increasing amounts of HspBP1. Aliquots were removed and assayed for activity. Activities are compared to luciferase renatured without HspBP1. Points are averages of triplicate assays and standard deviations were less than 5% of the mean.

DETAILED DESCRIPTION OF THE INVENTION

Unless defined otherwise, all technical and scientific terms used herein have the same meanings as commonly understood by those of ordinary skill in art of the invention. For example, see the definitions provided by U.S. Pat. No 5,955,312 by Hillman and Goli, which is incorporated herein by reference. All publications mentioned herein are incorporated by reference for the purpose of describing and disclosing the cell lines, vectors, and methodologies which might be used in connection with the invention.

The invention is based on the discovery of novel polynucleotides encoding two isoforms of human HspBP, and the use of these polynucleotides and proteins in discovering and isolating the homologous polynucleotides and proteins of several different species, including mouse, rat, and zebrafish.

The polynucleotides and proteins of the invention are useful for research on pathways in which active Hsp70 and related proteins participate, such as apoptosis, development, and signal transduction. Furthermore, the invention is useful in the research and in the treatment of maladies involving active Hsp70, such as various types of cancer and heart disease.

For example, it is known that hypoxic stress is a signal that increases the amount of Hsp70 in cardiac tissue, whereupon Hsp70 helps cells survive by binding to partially denatured proteins and assisting in the refolding of these proteins into more stable native structures. Such assistance would be extremely important in proving protection to the heart during periods of hypoxia such as during an infarct or during surgery when blood flow to the heart may be temporarily halted. Thus, discovering, characterizing, and devising ways to down-regulate the expression or activity of Hsp70-inhibiting proteins, such as the HspBP, is clearly useful.

It is also known that harmful conditions, including oxidative stress and UV radiation, can cause programmed cell death (apoptosis). Hsp72, a member of the Hsp70 family, has been shown to inhibit a signal transduction pathway leading to programmed cell death by preventing stress-induced activation of Jun N-terminal kinase, JNK. Gabai, V. L. et al. Hsp70 Prevents Activation of Stress Kinase. JBC 272:29, pp. 18033–18037 (Jul. 18, 1997). Moreover, Hsp70 is known to block the apoptotic process by blocking the activation of the caspase protease cascade. Mosser, D. D., et al., Role of the Human Heat Shock Protein Hsp70 in Protection Against Stress-Induced Apoptosis. Mol. and Cell. Biol., 17:9, pp. 5317–5327 (September, 1997). Thus, HspBP may play a role in promoting apoptosis by halting the inhibitory action of Hsp72 on JNK. By promoting apoptosis, HspBP may be useful in the killing of, for example, cancer cells.

Although many different methods and materials similar or equivalent to those described herein can be used in the practice or testing of the present invention, the preferred methods, devices, and material are now described.

The invention encompasses polypeptides comprising the amino acid sequences of SEQ ID NO:1 (HspBP-1; GenBank Acession Number AF093420) and SEQ ID NO:2 (HspBP-2; GenBank Acession Number AF187859). HspBP-1 is 359 amino acids long, while HspBP-2 is 362 amino acids in length. This difference in length is accounted for by the presence of 3 additional glycine residues in HspBP-2 at a glycine-rich region beginning at residue 25.

The invention also encompasses polynucleotides which encode HspBP. Thus, any nucleic acid sequence which encodes an amino acid sequence of a HspBP can be used to produce recombinant molecules which express HspBp. In a particular embodiment, the invention comprises the polynucleotide sequences encoding HspBP-1 (SEQ ID NO:3) and HspBP-2 (SEQ ID NO:4).

The invention further encompasses HspBP variants. A preferred variant is one having at least 90% amino acid sequence similarity to the HspBP amino acid sequences identified by SEQ ID NO:1 and SEQ ID NO:2. Most preferably, however, is a HspBP variant having at least 95% amino acid sequence similarity to SEQ ID NO:1 or SEQ ID NO:2.

As known by those skilled in the art, many commonly available computer programs can be used to search for sequence variants. For example, both the nucleotide and derived amino acid sequences of the human HspBP were used to search GenBank™, and no matches to known genes or proteins were found. However, when searching the GenBank™ EST data base with the programs BLAST and tBLASTn (National Center for Biotechnology Information), a number of significant matches were found in human, mouse, and rat sequences. None of these sequences were for known proteins.

Figure 2A:
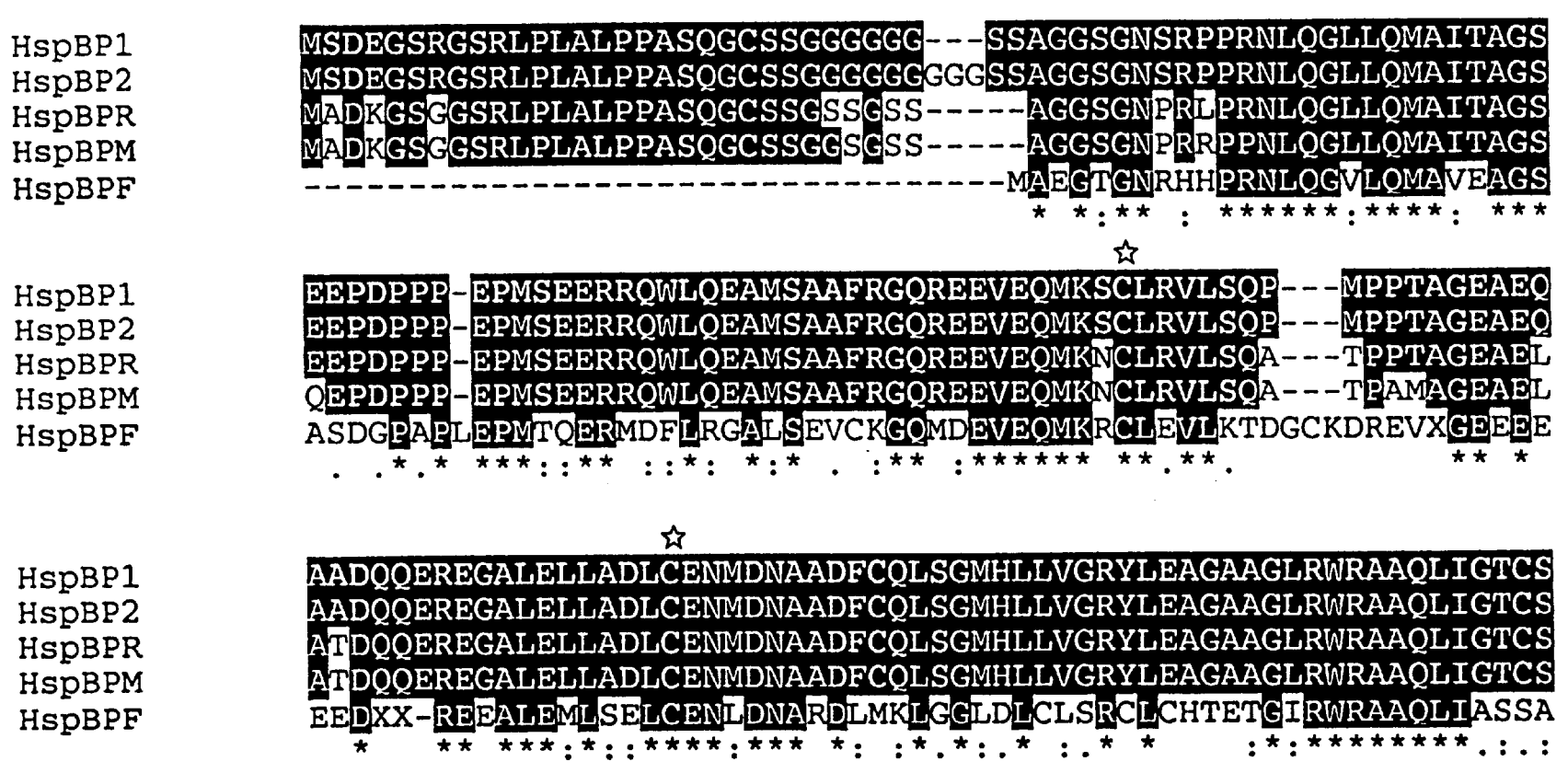
Figure 2B:
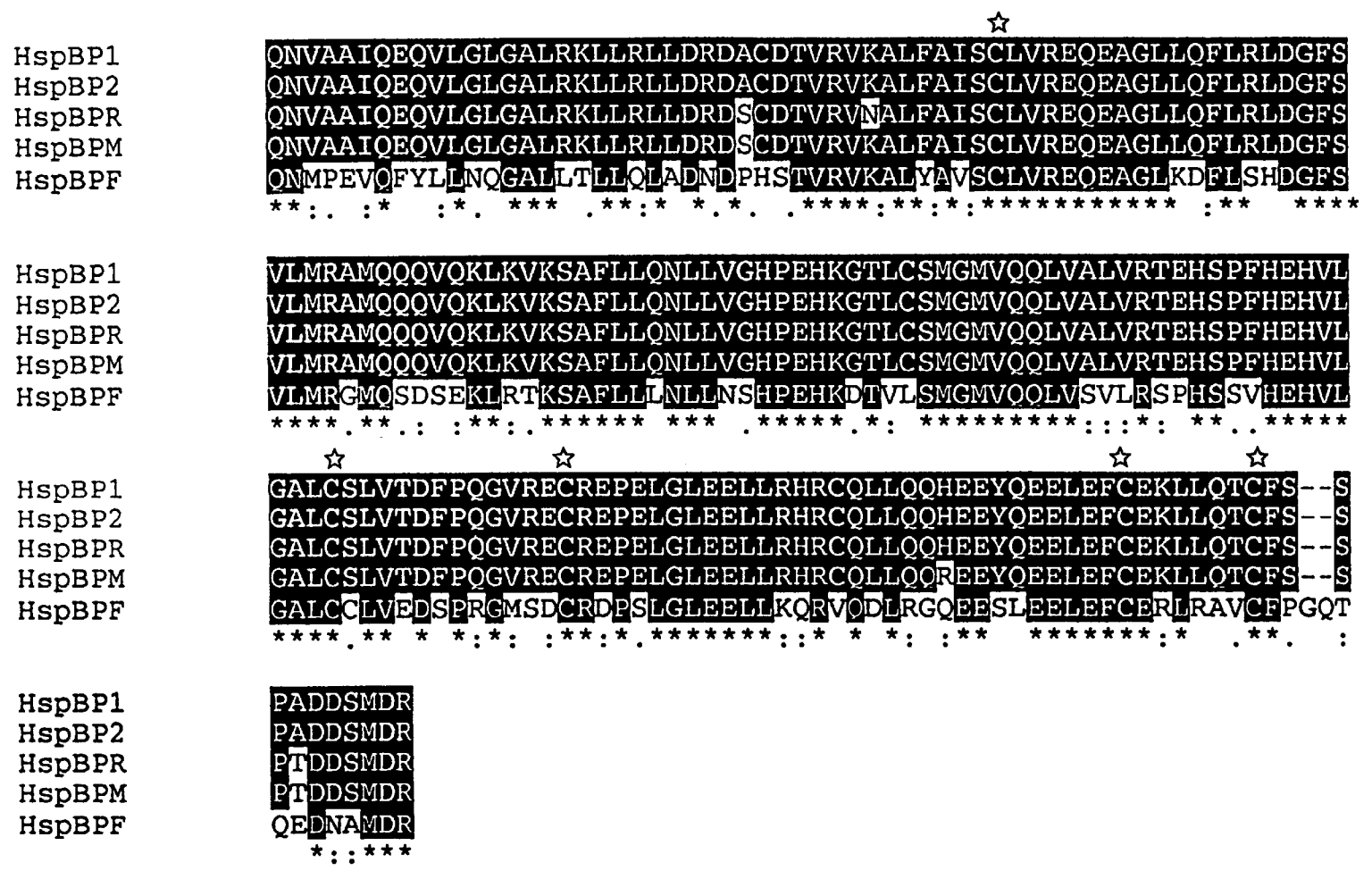

The deduced amino acid sequences of the HspBP of humans (HspBP-1; SEQ ID NO:1 and HspBP-2; SEQ ID NO:2), mice (HspBPM; SEQ ID NO:8), rats (HspBPR; SEQ ID NO:9), and zebrafish (HspBPF; SEQ ID NO:10) are shown in FIGS. 2A and 2B in alignment using the CLUSTALW computer program. As indicated by the black shading in FIGS. 2A and 2B, the amino acid sequences of HspBP for all species tested are highly conserved.

It will be appreciated by those skilled in the art that, as a result of the degeneracy of the genetic code, a multitude of HspBP-encoding nucleotide sequences, some bearing minimal homology to the nucleotide sequences of any known and naturally occurring gene, may be produced. The invention contemplates every possible variation of nucleotide sequence that could be made by selecting combinations based on possible codon choices. These combinations are made in accordance with the standard triplet genetic code as applied to the nucleotide sequence encoding naturally occurring HspBP, and all such variations are to be considered as being specifically disclosed.

Although nucleotide sequences which encode HspBP and their variants are preferably capable of hybridizing to the nucleotide sequence of the naturally occurring transcription sequences under appropriately selected conditions of stringency, it can be advantageous to produce nucleotide sequences encoding HspBP or their derivatives possessing a substantially different codon usage. For example, codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding HspBP and their derivatives without altering the encoded amino acid sequences include the production of RNA transcripts having more desirable properties, such as a greater stability or half-life, than transcripts produced from the naturally occurring sequence.

As known by one skilled in the art, a DNA sequence, or portions thereof, encoding HspBP and their derivatives may be produced entirely by synthetic chemistry. Subsequently, the synthetic nucleotide sequence may be inserted into any of the many available DNA vectors and cell systems using reagents that are commonly available. Moreover, synthetic chemistry may be used to introduce mutations into a sequence encoding HspBP or any portion thereof.

Also included within the scope of the invention are polynucleotide sequences that are capable of hybridizing to the nucleotide sequences of SEQ ID NO:3 or SEQ ID NO:4 under various conditions of stringency. Hybridization conditions are based on the melting temperature (Tm) of the nucleic acid binding complex or probe, as taught in Berger and Kimmel (1987, Guide to Molecular Cloning Techniques, Methods in Enzymology, v.152, Academic Press, San Diego, Calif.).

Natural, modified, or recombinant nucleic acid sequences may be ligated to a heterologous sequence to encode a fusion protein. One may, for example, screen a peptide library for inhibitors of HspBP activity by encoding a chimeric HspBP that can be detected by a commercially available antibody. In addition, a fusion protein may be engineered to contain a cleavage site located between the HspBP encoding sequence and the heterologous protein sequence, so that HspBP may be cleaved and purified away from the heterologous moiety.

Methods well known in the art can be used to construct expression vectors containing sequences encoding HspBP and appropriate transcriptional and translational control elements. Methods may include in vitro recombinant DNA techniques, synthetic techniques, and in vivo genetic recombination in a variety of expression vector/host systems, such as bacteria transformed with recombinant bacteriophage or plasmids or insect cell systems infected with viral expression vectors such as the baculovirus. These methods are described in standard laboratory references, such as Sambrook, J. et al. *Molecular Cloning, A Laboratory Manual,* Cold Spring Harbor Press, Plainview, N.Y. (1989).

Altered nucleic acids encoding HspBP which may be used in accordance with the invention include deletions, insertions or substitutions of different nucleotides resulting in a polynucleotide that encodes the same or a functionally equivalent HspBP. The protein may also show deletions, insertions or substitutions of amino acid residues which produce a silent change and result in functionally equivalent HspBP. Deliberate amino acid substitutions may be made on the basis of similarity in polarity, charge, solubility, hydrophobicity, hydrophilicity, and/or the amphipathic nature of the residues as long as the biological activity of HspBP is retained. For example, negatively charged amino acids aspartic acid and glutamic acid might be substituted for one another.

Also included within the scope of the invention are alleles encoding HspBP. As used herein, an "allele" or "allelic sequence" is an alternative form of the nucleic acid sequence encoding HspBP. Alleles result from a mutation, i.e. a change in the nucleic acid sequence, and generally produce altered mRNAs or polypeptides whose structure or function may or may not be altered. Any given gene may have none, one or many allelic forms. Common mutational changes which give rise to natural deletions, additions or substitutions of amino acids. Each of these types of changes may occur alone, or in combination with the others, one or more times in a given sequence.

Many ways exist in the art by which HspBP may be used therapeutically. Examples include, but are not limited to, administering HspBP through the introduction of an expression vector into a subject for in vivo therapy, administering a vector expressing antisense of a polynucleotide encoding HspBP, or administering HspBP as part of a pharmaceutical composition. Depending on the route of administration, appropriate agents for use in combination with HspBP for therapy may include any conventional pharmaceutical carrier such as saline or buffered saline (intravenous dosing) and dextrose or water (oral dosing). Further details on techniques for formulation and administration may be found in the latest edition of Remington's Pharmaceutical Sciences (Maack Publishing Co., Easton, Pa.).

In order to further illustrate the invention, the following example is provided. However, this example is not intended in any way to limit the invention.

EXAMPLE

Experimental Procedures

Screening of Yeast Library and cell cultures. The two-hybrid system was used to screen for Hsp70 interacting proteins. A portion of the cDNA for human Hsp70 (kindly provided by R. Morimoto, Northwestern University) coding for amino acids 1–351 was inserted into the yeast vector pAS2 (Clontech Laboratories, Palo Alto, Calif.) and used as the "bait plasmid" for the two-hybrid screening procedures. The yeast transfected with this plasmid expressed human Hsp70 as determined by Western blot analysis. These yeast would not grow on plates lacking histidine and were negative for β-galactosidase activity indicating that Hsp70 alone cannot activate the reporter genes and therefore will not result in false positives.

A human heart cDNA library (Clontech Laboratories, Palo Alto, Calif.) containing $3 \times 10^6$ independent clones was screened. This library was made in the pGAD10 cloning vector which had cDNAs fused to the activation domain (AD) of the GAL4 transcription activator. Methods for screening of the library were according to the manual provided by Clontech. Clones that lacked the DNA-BD/target plasmid but retained the AD/library plasmid were isolated using cycloheximide selection (Matchmaker Supplement Kit, Clontech). The candidate Leu$^+$, Trp$^-$ clones were then mated to Y187 (MATα) yeast strains carrying different test plasmids. Diploids from the mating were selected (Trp$^+$, Leu$^+$, His$^+$) and screened for the ability to produce β-galactosidase.

Lung adenocarcinoma cells (#3263) were kindly provided by the University of Arizona Cancer Center Cell Culture Core Facility. A cell pellet (approximately 100 µl) was frozen and thawed, suspended in an equal volume of 10 mM Tris-HCl (pH 7.4), 150 mM NaCl, 5 EDTA, 2 mM PMSF, centrifuged in a microfuge and the supernate was used for further analysis.

DNA Sequencing and Northern Blot Analysis. Plasmids were sequenced in both directions by the Laboratory of Molecular Systematics and Evolution at the University of Arizona. Oligonucleotides for sequencing were purchased from Genosys Biotechnologies (The Woodlands, Tex.). A Northern blot of human tissue mRNAs was purchased from Clontech Laboratories (Palo Alto, Calif.) and probed according to the procedure supplied by Clontech Laboratories using ExpressHyb hybridization solution. HspBP1 from nucleotide 457–1000, Hsp70 from nucleotide 841–1765 and Hsp40 from nucleotides 582–1043 were labeled and used as probes.

Bacterial Expression and Transcription/Translation. The cDNA for the ATP-binding domain of Hsp70 (amino acids 1–351) was inserted into the expression vector pET28a (Novagen, Madison, Wis.) minus the His-tag and expressed in bacteria. The protein was purified by solubilizing inclusion bodies in 6M guanidine HCl in binding buffer (0.5 M NaCl, 5 mM imidazole and 20 mM Tris-HCl ,pH 7.9) followed by dialysis against binding buffer.

The cDNA for HspBP1 was inserted into pET28a and expressed as a fusion protein containing the His-tag. Mutagensis by PCR was performed in pAS2 to create a NdeI site at the translation initiation region. The mutagenized fragment was subcloned into the TA vector (Invitrogen, Carlsbad, Calif.). Next, the original HspBP1 insert was removed from pAS2 by cutting with EcoRI and subcloning into the EcoRI site of pET28a. This was cut with NdeI and KpnI and this region was removed and replaced by the mutated fragment removed by digestion with NdeI and KpnI from the TA vector. The protein was purified over a His Bind affinity resin (Novagen, Madison, Wis.) following the manufacture's procedure with the addition of 0.5% NP40 to all buffers except the elution buffer.

To insert HspBP1 cDNA into the proper vector for coupled transcription/translation, the cDNA for HspBP1 was subcloned into pET5a using the Nde I and EcoR1 sites and coupled transcription/translation was done using the TNT T7 Quick Coupled Transcription/Translation System (Promega, Madison, Wis.) and [$^{35}$S]methionine (Amersham, Arlington Heights, Ill.)

Antibody Production and Western Blot Analysis. HspBP1 was prepared as described above and further purified by separation on a SDS polyacrylamide gel and the band was removed by electroelution. This preparation was used for antibody production. Antibodies were produced in rabbits by Animal Pharm Services, Inc. (Healdsburg, Calif.). Specific antibodies were purified from serum by initial affinity purification of IgG using a protein A column followed by an HspBP1 affinity column to purify specific antibodies.

SDS sample buffer was added to the lung adenocarcinoma cell lysate and the transcription/translation product. All samples were then heated at 95° C. for 5 min., centrifuged and the supernate was analyzed on a 12.5% SDS gel and transferred to nitrocellulose paper. The blot was blocked by incubation with Tris-saline (154 mM NaCl, 10 mM Tris, pH 7.5) containing 5% nonfat milk. Blots were then incubated with anti-HspBP1 antibody or preimmune IgG (0.1 μg/ml) overnight. Detection of antibody binding was performed using SuperSignal ULTRA (Pierce Chemical Co., Rockford , Ill).

Hsp70 Binding to HspBP1. The ATP-binding domain of Hsp70 (amino acids 1–351) was inserted into the expression vector pET28a (minus the His-tag), expressed in bacteria and purified by isolation of inclusion bodies. The truncated Hsp70 was incubated with or without the His-tagged HspBP1. These solutions were then incubated with a $Ni^{2+}$ affinity resin which binds the His-tagged HspBP1 and any associated proteins. HspBP1 alone or Hsp70 (1–351) alone were also incubated with the resin. The resin was centrifuged and washed several times with wash buffer. The bound proteins were eluted with 1M imidazole, 0.5M NaCl, 20 mM Tris-HCl (pH 7.9) and analyzed by Western blotting with both anti-6XHis antibody (Clontech Laboratories, Inc., Palo Alto, Calif.) and anti-Hsp70 antibody (StressGen, Victoria, BC).

Binding to proteins in a total homogenate was done by first binding His-tagged HspBP1 to the $Ni^{2+}$ affinity resin. A crude homogenate of bovine heart was prepared and incubated with the resin for 15 min. at 30° C. The resin was centrifuged and the pellets were saved. The resin was then rinsed several times with wash buffer and proteins were eluted by incubation with 1M imidazole buffer as above. The eluted proteins were analyzed by separation on polyacrylamide gels containing SDS and stained with Coomassie blue or Western blotted and probed with both anti-Hsp70 antibody and anti-6XHis antibody.

ATPase assays and ATP binding. ATPase assays were performed in 20 μM [β-$^{35}$S]ATP (0.631 mCi/μM), 4 mM Hepes, pH 7.4, 7.5 mM KCl, 0.45 mM MgAcetate and 80 μM DTT. Human recombinant Hsp70 (StressGen, Victoria, BC), HspBP1 and Hsp40 (kindly provided by Dr. E. Vierling, University of Arizona) were added at the indicated amounts. Assays were incubated at 37° C. and aliquots (1 μl) were removed at 0, 5, 10 and 15 min., spotted on PEI cellulose paper (J. T. Baker, Inc., Phillipsburg, N.J. ) and developed in 1M formic acid and 0.5M LiCl to separate ATP and ADP. Radioactivity was quantitated on a Packard Instant Imager (Meriden, Conn.). ATP binding was determined after 10 min., samples were removed (10 μl) and unbound nucleotides were removed using spin columns (ProbeQuant G-50, Pharmacia Biotech, Piscataway, N.J.). Bound nucleotides were processed as described above to separate ATP from ADP.

Renaturation of luciferase. Assays to measure the renaturation of luciferase in rabbit reticulocyte were done following the procedure of Schumacher et al. (1996) Biochemistry 35, 14889–14898. Luciferase (Sigma Chemical Co., St. Louis, Mo.) at 100 nM was dissolved in 25 mM tricine, pH 7.8, 8 mM Mg $SO_4$, 0.1 mM EDTA, 10 mg/ml bovine serum albumin, 10% glycerol, and 0.25% triton X-100. The protein was denatured by heating at 40° C. for 15 min. and then placed on ice. The enzyme was then diluted 10-fold by addition to rabbit reticulocyte lysate (Green Hectares, Oregon, Wis.) containing an ATP regeneration system and incubated at 25° C. for 90 min. Samples (5 μl) were removed and assayed for luciferase activity by addition to 120 μl of 25 mM tricine, pH 7.8, 8 mM $MgCl_2$, 0.1 mM EDTA, 12 mM DTT, 100 μM D-luciferin, 240 μM coenzyme A, and 0.5 mM ATP. Light production was measured in a Turner luminometer for 15 seconds.

Renaturation of recombinant firefly luciferase (Promega, Madison, Wis.) in a defined system was performed following the procedure of Johnson et al. (1998) J. Biol. Chem. 273, 3679–3686. Luciferase was diluted to 100 nM into above buffer and denatured by heating at 40° C. for 8 min and then placed on ice. The enzyme was then diluted 10-fold into 10 mM Tris, pH 7.5, 3 mM $MgCl_2$, 50 mM KCl and 2 mM dithiothreitol containing 800 nM human recombinant hsp70, 140 nM human recombinant Hsp90 alpha (StressGen, Victoria, BC), 160 nM Hsp40 and an ATP regenerating system and incubated at 25° C. for 4 hours. Samples were assayed as above.

Computer Analysis. Database searches were done using the BLAST server at the National Center for Biotechnology Information and the programs BLAST and tBLASTn. Isoelectric point and molecular weight determinations were done using the ExPASy molecular biology server at the Geneva University Hospital and University of Geneva, Geneva, Switzerland.

Results and Discussion

Isolation of cDNAs Using the Two-Hybrid System. A human heart cDNA library was screened and three colonies were isolated that grew on the trp⁻, leu⁻, his⁻ (triple minus) plates and were positive for β-galactosidase activity. Yeast containing the isolated library plasmids were mated to yeast containing the cDNA for the truncated Hsp70 and once again these colonies grew on the triple minus plates.and were positive for β-galactosidase activity. Mating of yeast containing the library plasmids with other controls (plasmid with no insert, plasmid with an insert other than Hsp70 ) did not produce colonies when grown on triple minus plates indicating that the interaction is specific for Hsp70 and the library plasmids.

Figure 1:
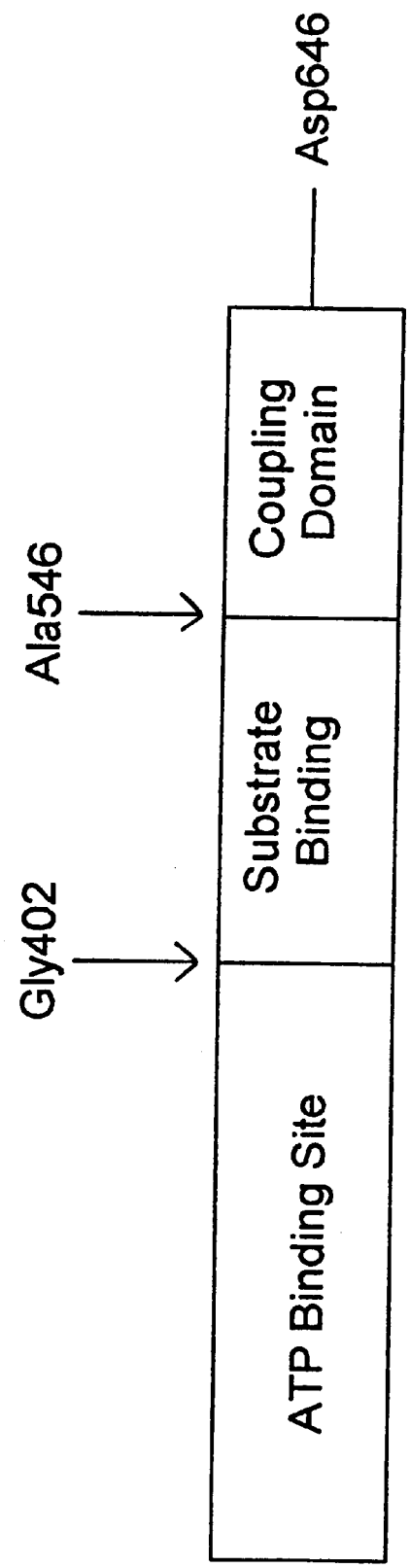
FIG. 1 is a schematic view of Hsp70 showing its three functional domains.

The cDNA insert sizes were 1.5, 1.6 and 1.6 kilobases. Nucleotide sequencing revealed open reading frames that code for proteins of approximately 40 kDa. Two of the clones were identical (HspBP2) and the third (HspBP1) differed in the coding region by having codons for 6 consecutive glycines whereas HspBP2 had codons for 9 glycines. HspBP2 also had two polyadenylation signals whereas HspBP1 had only the first polyadenylation signal. All results reported herein were done with HspBP1 (Seq. Listing No. 1). The sequence 5' to the initiation codon did not contain a termination codon therefore it was possible the coding region was not complete. Polymerase chain reaction (PCR) was used to amplify products from the plasmid library using a primer for a sequence 3' to the codons for the glycines and a primer in the flanking pGAD10 vectors. These experiments extended the sequence 53 bases to the 5'-end (underlined sequence in FIG. 1). This sequence lacked initiation codons in any reading frame but did contain a stop codon in the same reading frame as the open reading frame for the protein. Therefore, the first ATG after the stop codon has been assigned as the initiation codon. The calculated pI for the protein is 5.13 and the calculated molecular weight is 39,302. Both the nucleotide and derived amino acid sequences were used to search GenBank and no matches to known genes or proteins were found. However, when searching the GenBank EST database with the programs blast and tblastn, a number of significant matches were found in human, mouse and rat sequences. None of these sequences were for known proteins. The protein sequence was also analyzed for domain characteristics using a number of different programs and no similarities were found.

Figure 3:
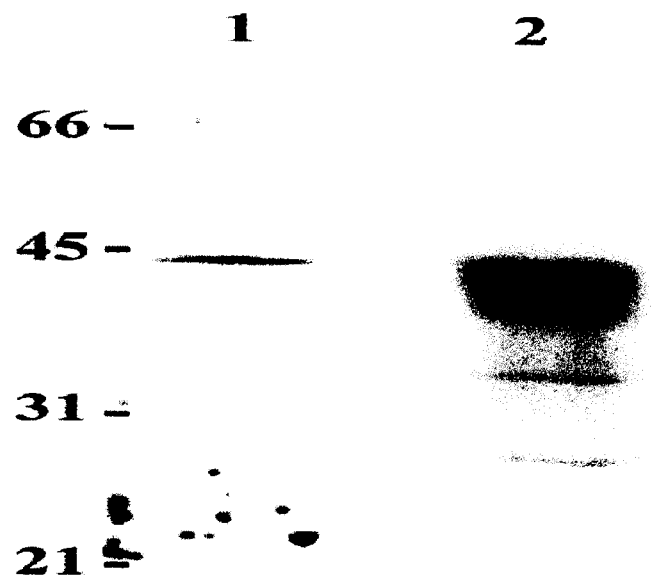
FIG. 3 shows a Western blot analysis of HspBP1. Proteins from a lung adenocarcinoma cell line (lane 1) and transcribed/translated HspBP1 (lane 2) and were separated on SDS polyacrylamide gels and transferred to nitrocellulose paper. Lane 1 was then incubated with anti-HspBP1 antibody and detection of antibody binding was performed using SuperSignal ULTRA (Pierce). Lane 2 was exposed to film to detect $^{35}S$ labeled proteins from the coupled transcription/translation. Numbers on the left side are molecular weight markers in kDa.

A polyclonal antibody against HspBP1 was prepared and used to detect HspBP1 in cell homogenates by western blots (FIG. 3). The cDNA for HspBP1 was transcribed and translated in vitro and this protein product was compared to the protein detected in cells. The recombinant HspBP1 has a slightly higher molecular weight due to additional amino acids including the His tag (not shown). The in vitro transcribed and translated product (lane 2) is the same size as the protein found in the cells (lane 1), confirming that the cDNA contains the entire protein coding region.

Figure 4:
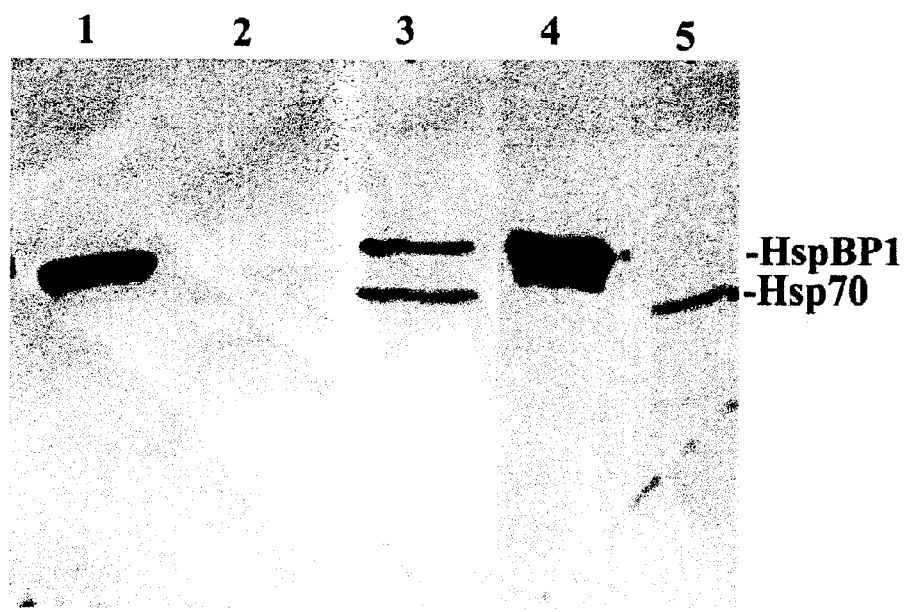
FIG. 4 shows the binding of HspBP1 to the ATP-binding domain of Hsp70. The ATP-binding fragment of Hsp70 (amino acids 1–351) was incubated with or without the His-tagged HspBP1. These solutions were then incubated with a $Ni^{2+}$ affinity resin which binds the His-tagged HspBP1 and any associated proteins. The resin was centrifuged and washed several times with wash buffer. The bound proteins were eluted with 1 M imidazole buffer and analyzed by Western blotting with both anti-6XHis antibody and anti-Hsp70 antibody. Hsp70 (1–351) bound to the resin only in the presence of HspBP1 (lane 3). Lane 1, HspBP1 alone on resin; lane 2, Hsp70 (1–351) alone on resin; lane 3, HspBP1 and Hsp70 (1–351); lane 4, HspBP1 standard; lane 5, Hsp70 (1–351) standard.
Figure 5:
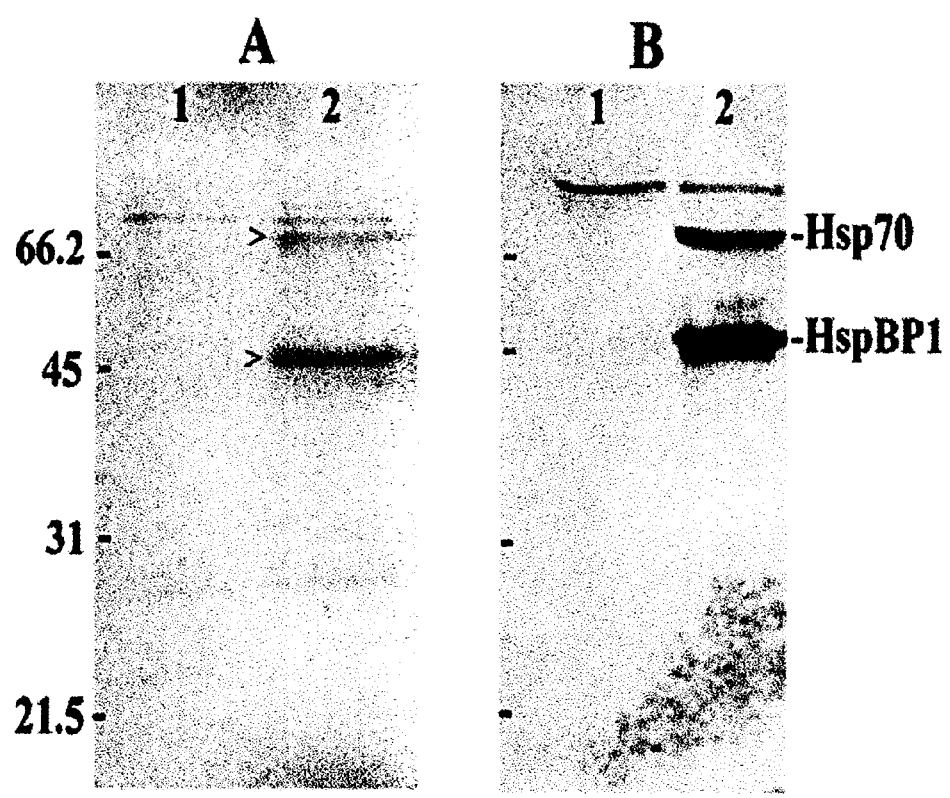
FIG. 5 shows HspBP1 binding to Hsp70 in a tissue homogenate. His-tagged HspBP1 was first bound to $Ni^{2+}$ affinity resin. A crude homogenate of bovine heart was prepared and incubated with the resin for 15 min. at 30° C. The resin was centrifuged and the supernates were saved. The resin was then rinsed several times with buffer and proteins were eluted by incubation with 1M imidazole buffer. The eluted proteins were analyzed by separation on polyacrylamide gels containing SDS and stained with Coomassie blue (Panel A) or Western blotted and probed with both anti-Hsp70 antibody and anti-6XHis antibody (Panel B). Lane 1 contains proteins eluted from resin without HspBP1 bound and Lane 2 contains proteins eluted from resin with HspBP1 bound.

A fragment of Hsp70 (amino acids 1–351) identical to the ATPase domain that was used in screening the yeast library was expressed in bacteria and purified. The fragment bound to a $Ni^{2+}$ affinity column in the presence of His-tagged HspBP1 (FIG. 4, lane 3) providing further evidence for an interaction between HspBP1 and the ATPase domain of Hsp70. The fragment was not retained on the column in the absence of HspBP1 (FIG. 4, lane 2). In a second set of experiments, His-tagged HspBP1 was first bound to the $Ni^{2+}$affinity resin and binding to proteins in a homogenate of bovine heart was determined. Western blotting revealed a strong immunoreactive band for Hsp70 that was eluted from the resin when HspBP1 was first bound (FIG. 5, panel B, lane 2). This band was absent if HspBP1 was not bound to the resin first (FIG. 5, panel B, lane 1). Further analysis on a lower percentage gel resolved the Hsp70 into two bands (not shown), which is consistent with both Hsp70 and Hsc70 binding to HspBP1. An additional immunoreactive band larger than Hsp70 is eluted in the presence or absence of HspBP1. This protein binds to the resin nonspecifically and reacts with the anti-Hsp70 antibody and could not be detected by protein staining (panel A). Protein staining revealed both the eluted HspBP1 (Panel A, lower arrow) and Hsp70 (upper arrow). Additional bands are present above Hsp70 and below HspBP1 and are eluted in the presence or absence of HspBP1.

Figure 6:
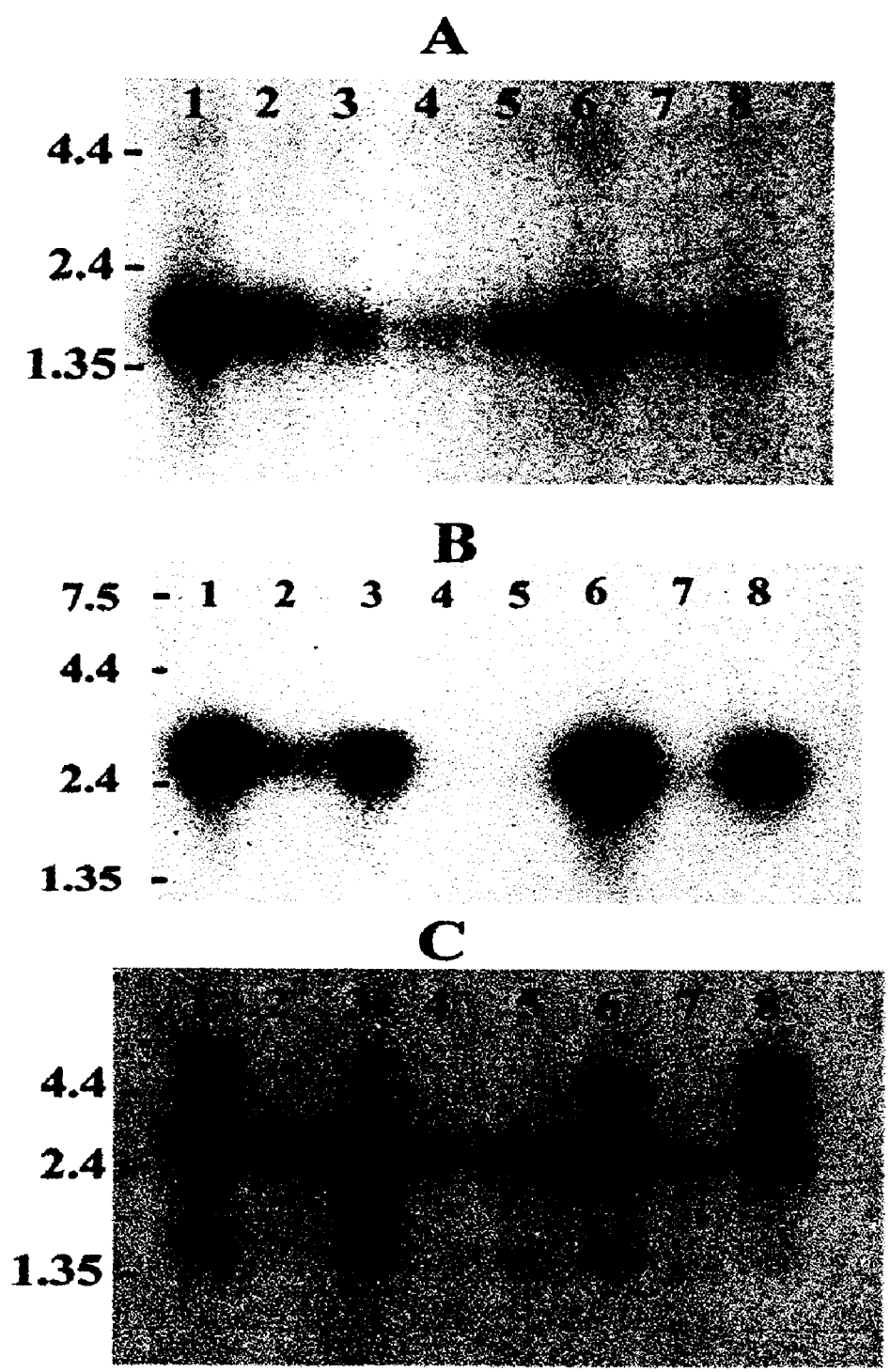
FIG. 6 shows a Northern blot of poly $A^+$ RNAs from human tissues. A Northern blot (Clontech Lab., Inc.) containing poly $A^+$ RNA from human heart (1), brain (2), placenta (3), lung (4), liver (5), skeletal muscle (6), kidney (7) and pancreas (8) was probed with either human HspBP1 cDNA (panel A), Hsp70 cDNA (panel B) or Hsp40 cDNA (panel C). Numbers on the left are molecular weight markers in kilobases.

A Northern blot of human tissues (FIG. 6) was probed with a region of HspBP1 cDNA (panel A), Hsp70 cDNA (panel B) and Hsp40 cDNA (panel C). Heart and skeletal muscle contain the highest amounts of HspBP1 mRNA. These two tissues also exhibit relatively high levels of Hsp70 and Hsp40 mRNAs. However, there is not a consistent correlation between the amount of HspBP1, Hsp70 and Hsp40 mRNAs in the other tissues. These results suggest that there is a tissue specific expression of HspBP1 and this expression is not dependent on the amount of Hsp70 or Hsp40 mRNA. In all tissues the size of the HspBP1 mRNA is approximately 1.7 kb.

Figure 7:
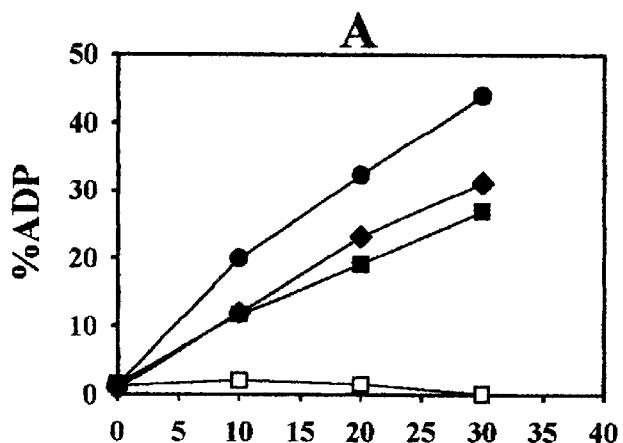
FIG. 7 shows the effect of HspBP1 on Hsp70 ATPase activity. ATPase activity was determined using 1.4 $\mu M$ Hsp70, 7.9 $\mu M$ HspBP1 and 16.5 nM Hsp40. Effects of HspBP1 on Hsp70 ATPase activity (A) and Hsp40 stimulated activity (B) were determined as described in the Experimental Procedures section of the Detailed Description. The blank control, endogenous Hsp70, and HspPB1 activities were subtracted to determine the effect on the Hsp40 stimulated Hsp70 activity (C). ●, Hsp70+Hsp40; ◆ Hsp70+HspBP1; ○, Hsp70+Hsp40+HspBP1; ■, Hsp70 alone; ▲HspBP1 alone; □, blank.
Figure 7:
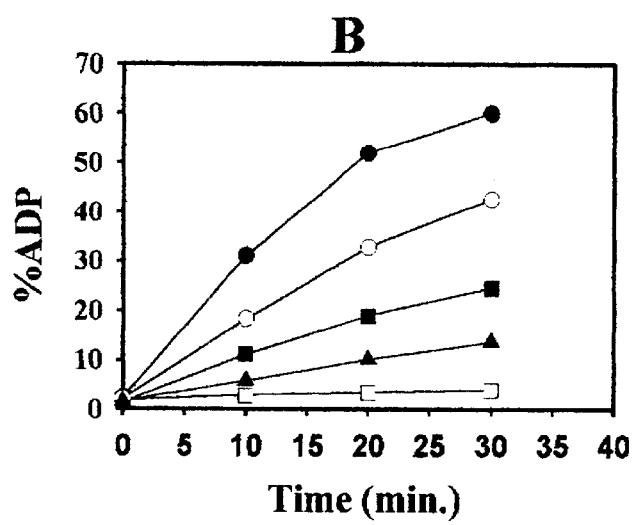
Figure 7:
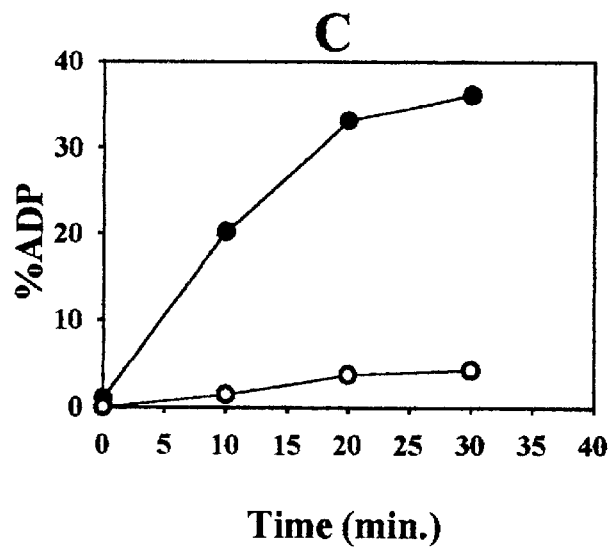

The next series of experiments were conducted to determine the effect of HspBP1 on Hsp70 enzymatic activity. HspBP1 had a slight stimulatory effect on the Hsp70 ATPase activity in the absence of Hsp40 (FIG. 7, panel A) but this is due to the low ATPase activity found in the HspBP1 preparations (FIG. 7, panel B). This is most likely a contaminant that varies in different preparations. The Hsp70 ATPase could be stimulated by Hsp40 (FIG. 7, panels A,B) and this increase in activity was inhibited by HspBP1 (FIG. 7, panel B). The ATPase activities for Hsp70 and HspBP1 alone were subtracted from the activity of Hsp70+Hsp 40+HspBP1 to determine the effect on the Hsp40 stimulated activity (FIG. 7, panel C). These data clearly indicate that HspBP1 inhibits the Hsp40 stimulation of Hsp70 activity.

The effect of HspBP1 on nucleotide binding to Hsp70 under steady-state conditions was next examined to explore the mechanism by which HspBP1 inhibits Hsp70 ATPase. In the absence of Hsp40 , the majority of nucleotide bound to Hsp70 is in the form of ATP which is consistent with an unstimulated ATPase activity (FIG. 8). HspBP1 inhibited nucleotide binding by approximately 30% and this was due to a decrease in ATP binding. In the presence of Hsp40, the total amount of nucleotide binding doubles and the ratio of ADP to ATP increases, consistent with a stimulation of ATPase activity, the production of ADP and ATP turnover. In the presence of HspBP1 and Hsp40 the amount of total nucleotide bound decreased to half the amount and this is due to a decrease in both ATP and ADP bound. These results are consistent with a decrease in ATP binding which would decrease the amount of nucleotide available for hydrolysis and therefore result in a decrease in ADP bound. We conclude from these experiments that the inhibition in Hsp70 ATPase activity by HspBP1 is due to a decrease in ATP binding.

The ADP form of Hsp70 binds substrate whereas the ATP form cannot, therefore a decrease in ATP binding and an inhibition of Hsp40 stimulated ATPase suggests that HspBP1 could inhibit the ability of Hsp70 to renature a substrate. Reticulocyte lysate contains the necessary components including Hsp70 for renaturation of denatured firefly luciferase. The effect of HspBP1 on Hsp70-dependent protein renaturation was analyzed using this system. Experiments were done with varying concentrations of HspBP1 and measuring the amount of luciferase renatured after 90 min. (FIG. 9, panel A). HspBP1 inhibited renaturation of luciferase with a half-maximal inhibition at 2 $\mu$M. The reticulocyte lysate is an undefined system containing many unknown proteins, therefore, similar refolding experiments were done in a defined system as described by Johnson et al. (1998) *J. Biol. Chem.* 273, 3679–3686. In the defined system HspBP1 again inhibited renaturation of luciferase is a dose-dependent manner with a similar half-maximal inhibition concentration (FIG. 8, panel B). Maximum inhibition was approximately 50% whereas in the recticulocyte lysate inhibition was over 90%. These experiments were done with different sources of luciferase and this may explain the difference. These data indicate a relatively tight interaction of HspBP1 with Hsp70. As a comparison, the dissociation constant for auxilin (an activator of Hsc70 ATPase activity) with Hsc70 was determined to be 0.6 $\mu$M (13).

Recently, numerous proteins have been identified as regulators of Hsp70 mediated renaturation of misfolded proteins indicating that this is a complex system that is far from clearly defined. The findings reported in this paper increase this complexity by the addition of another protein (HspBP1) that may have potential in vivo regulatory properties of Hsp70. Proper functioning of Hsp70 as a protein chaperone is dependent on its bound nucleotide state. The ATP form of the protein binds substrate very poorly and therefore must be converted to the ADP form before the misfolded protein can bind. This conversion is catalyzed by another heat stress protein named Hsp40. As reported here, HspBP1 inhibits the Hsp40 stimulated Hsp70 ATPase by inhibiting ATP binding therefore blocking the production of ADP. The end result is the inhibition of Hsp70 mediated refolding as seen in the HspBP1 inhibition of renaturation of denatured luciferase in the rabbit reticulocyte lysate and in a defined system. Other regulators of Hsp70 activity affect ADP binding. For example, Hip stimulates the renaturation of a denatured substrate by decreasing the release of ADP, whereas BAG-1 inhibits Hsp70 activity by increasing the release of ADP.

The Northern blot analysis indicates that heart and skeletal muscle contain the highest amounts of HspBP1 mRNA. It is not known if this reflects the relative amounts of the protein in these tissues. A high amount in heart muscle does pose some interesting speculation as to the function in this tissue. Recent studies in Xenopus have reported that the heart is the most thermal sensitive of the organs examined with respect to activation of heat shock transcription factor (HSF) binding and an increase in Hsp70 mRNA and protein levels. HspBP1 may bind to the endogenous Hsp70 rendering it inactive and thereby cause a feedback mechanism whereby the cell senses a lower amount of active Hsp70 and results in an increased Hsp70 expression. Through this mechanism the heart would have lower levels of active Hsp70 and therefore a lower amount of stress would be required to activate synthesis of more Hsp70.

The experiments reported here indicate that HspBP1 may regulate Hsp70 mediated refolding of denatured proteins, however, it remains to be seen if this is the in vivo function. It is possible that HspBP1 may be involved in other Hsp70 regulated activities such as apoptosis via the stress activated protein kinase pathway (SAPK). For instance, cell death caused by tumor necrosis factor (TNF) can be prevented by overproduction of Hsp70 (24). Recently, others have provided evidence that Hsp70 can inhibit the activation of Jun N-terminal kinase (JNK) and thereby inhibit phosphorylation of c-JUN by JNK resulting in an inhibition of apoptosis via this pathway. Further down this pathway, Hsp70 has been shown to inhibit the processing of caspase-3 from the inactive pro-caspase and thereby inhibiting the proteolytic activity of this enzyme and cell death. These, then, are potential parts of the pathway that may be regulated by HspBP1.

While this example is contemplated to be the preferred mode, it will be understood by those in the art that numerous alternative methodologies may be successfully practiced in lieu of the preferred method described herein.

We claim:

1. An isolated and purified sequence of polynucleotides encoding a polypeptide as disclosed in any one of SEQ ID NO: 1, 2, 8 or 9, wherein said polypeptide binds a heat-shock protein and inhibits an ATPase activity of said heat-shock protein.

2. An isolated and purified sequence of polynucleotides encoding a polypeptide that binds a heat-shock protein and inhibits an ATPase activity of said heat-shock protein, wherein said isolated and purified sequence of polynucleotides is selected from the group consisting of SEQ ID No. 3, SEQ ID No. 4, SEQ ID No. 5 and SEQ ID No. 6.

3. The sequence of claim 1, wherein said heat-shock protein is heat-shock protein 70.

4. An isolated and purified polynucleotide sequence, said polynucleotide sequence encoding the amino acid sequence of SEQ ID NO: 1.

5. A hybridization probe comprising the polynucleotide sequence of claim 4 and a detectable label.

6. A polynucleotide fragment which is fully complementary to the polynucleotide sequence of claim 4.

7. A hybridization probe comprising the polynucleotide fragment of claim 6 and a detectable label.

8. An expression vector containing the polynucleotide sequence of claim 4.

9. A host cell line containing the expression vector of claim 8.

10. An isolated and purified polynucleotide sequence, said polynucleotide sequence encoding the amino acid sequence of SEQ ID NO:2.

11. A hybridization probe comprising the polynucleotide sequence of claim 10 and a detectable label.

12. A polynucleotide fragment which is fully complementary to the polynucleotide sequence of claim 10.

13. A hybridization probe comprising the polynucleotide fragment of claim 12 and a detectable label.

14. An expression vector containing the polynucleotide sequence of claim 10.

15. A host cell line containing the expression vector of claim 14.

16. The sequence of claim 1, said sequence of polynucleotides comprising SEQ ID No: 3.

17. The sequence of claim 1, said sequence of polynucleotides comprising SEQ ID No: 4.

* * * * *